United States Patent [19]

Vander Heyden

[11] Patent Number: 5,323,657
[45] Date of Patent: * Jun. 28, 1994

[54] VOLUMETRIC FLOW CORRECTOR AND METHOD

[75] Inventor: William H. Vander Heyden, Mequon, Wis.

[73] Assignee: Badger Meter, Inc., Milwaukee, Wis.

[ * ] Notice: The portion of the term of this patent subsequent to Apr. 13, 2010 has been disclaimed.

[21] Appl. No.: 9,481

[22] Filed: Jan. 25, 1993

Related U.S. Application Data

[63] Continuation-in-part of Ser. No. 793,753, Nov. 18, 1991, Pat. No. 5,201,581, and a continuation-in-part of Ser. No. 787,188, Nov. 4, 1991, Pat. No. 5,226,728.

[51] Int. Cl.$^5$ .................. G01F 15/04; G01N 25/22
[52] U.S. Cl. ........................... 73/861.02; 73/195; 73/863.03; 73/863.61; 374/36
[58] Field of Search ............... 374/36, 37; 73/196, 73/863.03, 863.61, 861.02, 861.03, 202, 195

[56] References Cited

U.S. PATENT DOCUMENTS

| | | | |
|---|---|---|---|
| 3,559,482 | 2/1971 | Baker et al. | 73/202 |
| 3,701,280 | 10/1972 | Stroman | 73/861.03 |
| 3,777,562 | 12/1973 | Clingman | 374/37 |
| 4,062,236 | 12/1977 | Clingman | 374/37 |
| 4,125,018 | 11/1978 | Clingman | 374/37 |
| 4,125,123 | 11/1978 | Clingman | 374/37 |
| 4,285,245 | 8/1981 | Kennedy | 73/861 |
| 4,351,614 | 9/1982 | Garnier | 374/37 |
| 4,380,400 | 4/1983 | Searle | 374/37 |
| 4,396,299 | 8/1983 | Clingman et al. | 374/37 |
| 4,446,748 | 5/1984 | Clingman et al. | 73/863.03 |
| 4,527,435 | 7/1985 | Hall et al. | 73/863.03 |
| 4,562,744 | 1/1986 | Hall et al. | 73/861.02 |
| 4,584,868 | 4/1986 | Jacobsen et al. | 73/861.03 |
| 4,590,790 | 5/1986 | Hicks et al. | 73/202 |
| 4,614,721 | 9/1986 | Goldberg | 374/37 |
| 4,677,841 | 7/1987 | Kennedy | 73/30 |
| 4,845,976 | 7/1989 | Johnson et al. | 374/36 |
| 5,016,482 | 5/1991 | Clingman et al. | 73/863.61 |
| 5,115,687 | 5/1992 | Clingman, Jr. et al. | 73/863.03 |
| 5,201,581 | 4/1993 | Vander Heyden et al. | 374/36 |
| 5,226,728 | 7/1993 | Vander Heyden | 374/36 |

FOREIGN PATENT DOCUMENTS

| | | | |
|---|---|---|---|
| 0864113 | 2/1971 | Canada | 73/196 |
| 0326494 | 8/1989 | European Pat. Off. | 374/37 |
| 1110893 | 7/1961 | Fed. Rep. of Germany | 73/196 |
| 0000447 | 1/1980 | Japan | 73/861.03 |
| 0065117 | 5/1980 | Japan | 73/202 |
| 2099589 | 12/1982 | United Kingdom | 374/36 |

*Primary Examiner*—Diego F. F. Gutierrez
*Attorney, Agent, or Firm*—Quarles & Brady

[57] ABSTRACT

A method and apparatus for measuring a base condition volumetric flowrate of a pipeline gas flowing through a pipeline in which a pipeline gas flowrate is measured by a pipeline gas flowmeter that responds to density in a characteristic manner, a sample gas flowrate is measured by a sample gas flowmeter that responds to density in the same manner as a pipeline gas flowmeter, and a base condition sample gas volumetric flowrate is measured by measuring the base condition energy flowrate of the sample gas, measuring the base condition heating value of the sample gas and dividing the base condition energy flowrate by the base condition heating value. The measured pipeline gas flowrate through the pipeline is then adjusted by the ratio of the base condition sample gas flowrate divided by the measured flowrate of the sample gas. The temperature of the sample gas should be substantially the same as the pipeline gas in the pipeline when the sample gas flowrate is measured.

15 Claims, 10 Drawing Sheets

FIG. 5
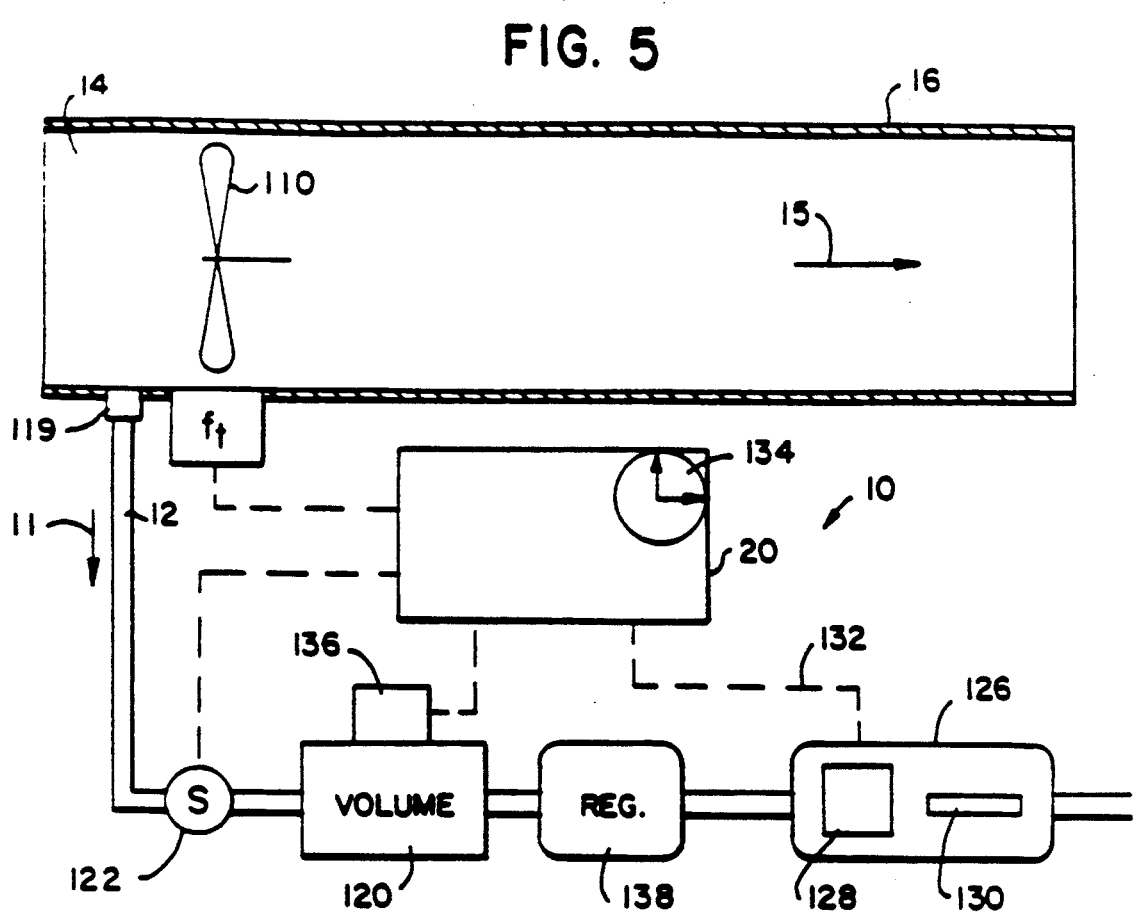
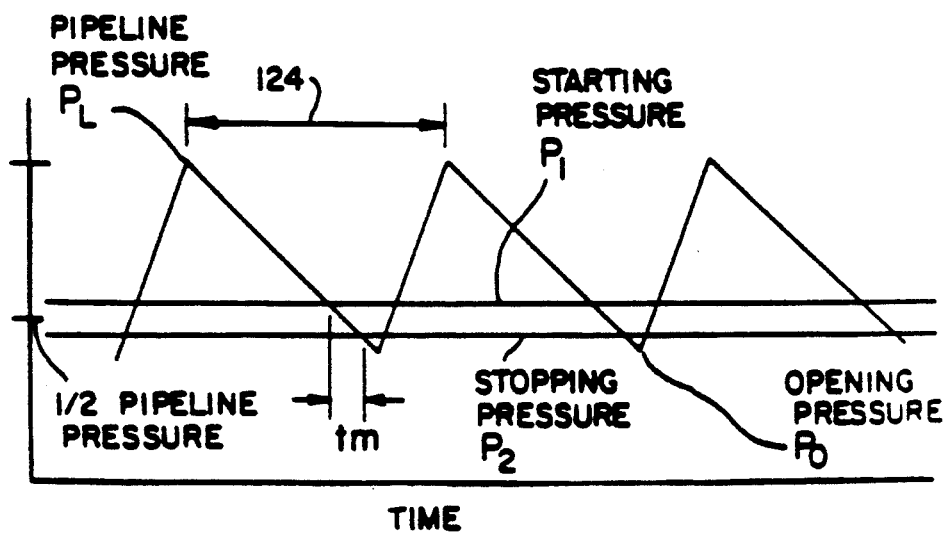
SAMPLE GAS PRESSURE IN FIRST CHAMBER
FIG. 6

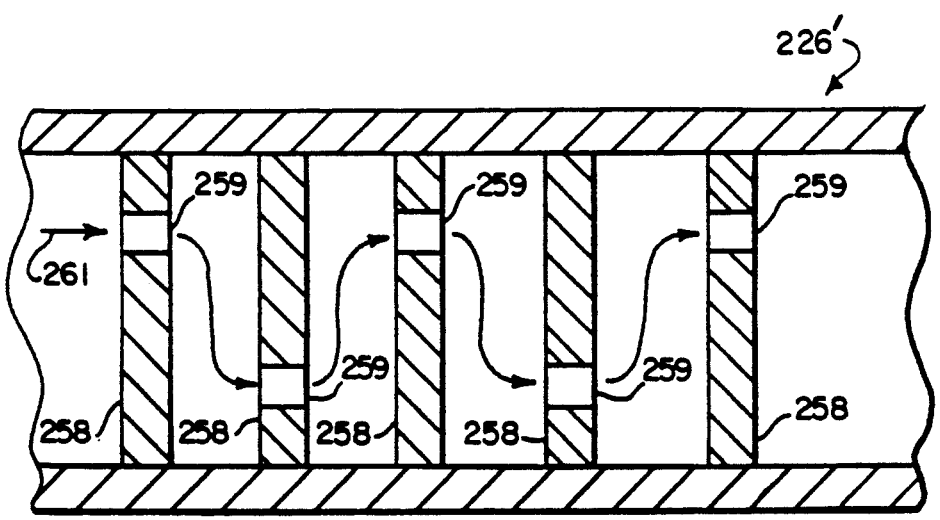
FIG. 12
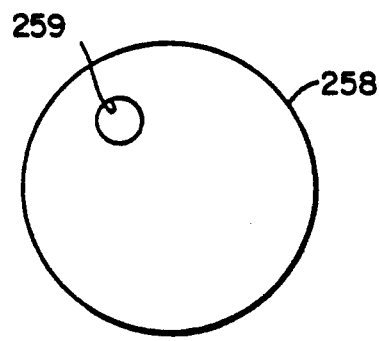
FIG. 13
FIG. 14
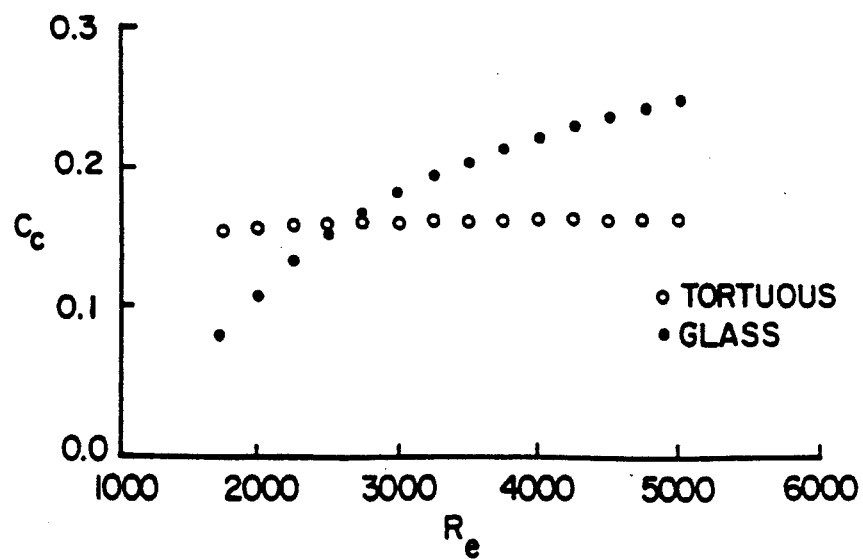

VOLUMETRIC FLOW CORRECTOR AND METHOD

This application is a continuation-in-part of patent application Ser. No. 07/793,753, filed Nov. 18, 1991, now U.S. Pat. No. 5,201,581, and a continuation-in-part of patent application Ser. No. 07/787,188, filed Nov. 4, 1991, now U.S. Pat. No. 5,226,728. Both application Ser. Nos. 07/793,753 and 07/787,188 are assigned to the assignee of this application.

FIELD OF THE INVENTION

The present invention relates to the real time measurement of mass and energy flowrates through a pipeline. Particularly, the invention relates to a method and apparatus that derives an adjusted or base condition volumetric flowrate $Q_b$ of a pipeline gas flowing through a pipeline which is adjusted to correspond to the energy flowrate of the pipeline gas. As such, the adjusted volumetric flowrate $Q_b$ can be represented as a corresponding volumetric flowrate at a defined base pressure and temperature which has an equivalent energy flowrate.

BACKGROUND OF THE INVENTION

In gaseous flows, the phenomena of compression exists and has a large effect. It allows the number of molecules for a given volume to change with pressure and temperature as well as with composition. Therefore, it is desirable to make natural gas sales transactions either by mass, energy, or at standard pressure and temperature conditions. In the U.S., for example, the standard pressure and temperature of gas is stated as 14.7 psia and 60° F. for many transactions. Delivery calculations state the flow adjusted to correspond to these base conditions even though the actual gas in the transaction is probably at a different pressure or temperature. A piece of equipment designed to accomplish the task of converting a measured volumetric flowrate to a base volumetric flowrate at a defined pressure and temperature is referred to as a "volume corrector".

In the traditional method of gas measurement, a volume correction ratio $$\frac{Q_b}{Q_f}$$

is determined from the pipeline gas flow temperature, pressure, and composition using the following relation:

$$\frac{Q_b}{Q_f} = \frac{T_b}{T_f} \frac{P_f}{P_b} \frac{Z_b}{Z_f} \quad (1)$$

where $Q_f$ is the measured volumetric flowrate of the pipeline gas through the pipeline, $T_b$ and $P_b$ are the base condition temperature and pressure (e.g. 14.7 psia and 60° F.), $T_f$ and $P_f$ are the measured flow temperature and pressure of the pipeline gas in the pipeline, $Z_b$ and $Z_f$ are the supercompressibility factors at the base condition and the flow condition, respectively, and $Q_b$ is the base condition volumetric flowrate. Such a calculation is typically carried out in a flow computer.

Using the relation in Eq. (1) to compute base condition volumetric flowrate $Q_b$ requires high accuracy in the measurement of the flow temperature $T_f$ and pressure $P_f$. This requires that pressure and temperature sensors for monitoring $P_f$ and $T_f$ be calibrated frequently.

The ratio $$\frac{Z_b}{Z_f}$$

in Eq. (1) presents even more difficulties. The composition of the gas is normally measured by gas chromatography and the supercompressibilities, $Z_b$ and $Z_f$, are estimated from either the virial equations of state, or from pre-calculated correlations such as NX-19 or the more recent Gergg Equations. Alternatively, a meter that measures heating value, relative density, %$CO_2$ and %$N_2$ can be used to calculate the ratio $$\frac{Z_b}{Z_f}.$$

This is because the Gergg Equations in their short form allow calculation of the ratio $$\frac{Z_b}{Z_f}$$

from these parameters.

Knowledge of the values of the virial coefficients of particular gas compositions is quite limited so calculation of supercompressibility from the virial equation of state is not always possible. The Gergg Equations and NX-19 correlation are mathematical models obtained by mapping known and measured properties. The Gergg Equations, in particular, are very good over a wide range of compositions. Use of the Gergg Equations, however, requires either a chromatograph or a special meter to measure the properties needed to solve the short form Gergg Equations, both of which are expensive.

It is, therefore, difficult to obtain accurate measurement of the supercompressibility ratio $$\frac{Z_b}{Z_f}$$

in a cost effective manner.

Each of the measurements discussed above (volumetric flow, temperature, pressure, composition, and/or energy content) also introduce an opportunity for measurement error. While the Gergg Equations are regarded as accurate, the aggregation of measurement errors can be quite substantial and can distort calculations. To minimize measurement errors, each piece of instrumentation must be maintained and calibrated periodically. But, even then, additional inaccuracy can accrue in the flow computer from calculations or inaccurate formulas or correlations.

The result is that present day equipment cannot accurately measure energy flowrates, or volume correction ratios $$\frac{Q_b}{Q_f}$$

in a cost effective manner.

The present invention alleviates the need to compute the supercompressibility of the pipeline gas. It also alleviates the need to measure the absolute temperature, absolute pressure, and composition of the pipeline gas. The present invention, therefore, operates much more accurately to determine energy flowrates, volume correction ratios $$\frac{Q_b}{Q_f},$$

and adjusted or base condition volumetric flowrates $Q_b$.

SUMMARY OF THE INVENTION

The present invention is a method and apparatus for measuring a base condition volumetric flowrate $Q_b$ of a pipeline gas flowing through a pipeline which corresponds to a volumetric flowrate at a base condition pressure and temperature.

The method involves measuring a flowrate $Q_f$ of the pipeline gas flowing through the pipeline with a pipeline gas flowmeter. The pipeline gas flowmeter should respond to density and density effects in a characteristic manner. It further involves flowing sample gas from the pipeline to a sample gas flowmeter, where the sample gas flowmeter responds to density and density effects in the same manner as the pipeline gas flowmeter. The flowrate of the sample gas $Q_f'$ is measured with the sample gas flowmeter. The temperature of the sample gas in the sample gas flowmeter is kept substantially at the same temperature as the pipeline gas in the pipeline.

The method also involves measuring a base condition sample gas volumetric flowrate $Q_b'$. This is done by measuring a base condition energy flowrate (energy per unit time) of the sample gas $E_{sample\ gas}$, measuring a base condition heating value (energy per unit volume) of the sample gas $H_{sample\ gas}$ and dividing the base condition sample gas energy flowrate $E_{sample\ gas}$ by the base condition sample gas heating value $H_{sample\ gas}$.

A correction ratio $$\left(\frac{Q_b'}{Q_f'}\right)$$

is then calculated and used to adjust the flowrate $Q_f$ of the pipeline gas flowing through the pipeline to determine the base condition base volumetric flowrate $Q_b$ of pipeline gas through the pipeline.

The method also contemplates splitting the flow of sample gas into a waste stream and a test stream after the sample gas flowrate $Q_f'$ has been measured by the sample gas flowmeter and before the base condition sample gas volumetric flowrate $Q_b'$ has been measured. If the flow is split into a known ratio, the base condition sample gas energy flowrate $E_{sample\ gas}$ can be measured by measuring the base condition energy flowrate of the test stream and multiplying by the ratio of the mass flowrate of the entire sample gas stream compared to the flowrate of the test stream.

The preferred way of measuring the base condition energy flowrate $E_{sample\ gas}$ of the sample gas involves flowing sample gas from the sample gas flowmeter to a burner; burning the sample gas in the burner with air flowing to the burner; adjusting the air flowrate to the burner so that the sample gas burns at a maximum flame temperature; and determining the adjusted air flow rate; and determining the base condition sample gas energy flowrate $E_{sample\ gas}$ from the adjusted air flowrate. This can be done because the base condition energy flowrate is directly proportional to the adjusted air flowrate under conditions where flame temperature is maximized.

The base condition sample gas energy flowrate $E_{sample\ gas}$ can also be derived, without adjusting the air flowrate to the burner, by adjusting the flowrate of sample gas to the burner $Q_b'$ such that the flame burns at maximum temperature.

The preferred method of measuring the base condition heating value of the sample gas $H_{sample\ gas}$ involves intermittently flowing a reference gas to the burner and measuring flowrates at maximum flame temperature for both the sample gas and the reference gas. The base condition sample gas heating value $H_{sample\ gas}$ is related to the base condition heating value for the reference gas $H_{reference\ gas}$ by the ratio of the flowrates of the gases to the burner $$\left(\frac{Q_{reference\ gas}}{Q_{sample\ gas}}\right).$$

Also, the value can be adjusted if the airflow to the burner is changed. The preferred method for determining the ratio of the flowrates to the burner $$\left(\frac{Q_{reference\ gas}}{Q_{sample\ gas}}\right)$$

involves filling a chamber with sample gas, flowing the sample gas from the chamber, and measuring a time rate of change of sample gas pressure at a measuring pressure as a sample gas flows from the chamber. Then filling the chamber with reference gas, flowing the reference gas from the chamber, and measuring a time rate of change of reference gas pressure as reference gas flows from the chamber at substantially the same measuring pressure as the sample gas. Finally, the time rate of change of the sample gas pressure is divided by the time rate of change of the reference gas pressure to determine the ratio $$\left(\frac{Q_{reference\ gas}}{Q_{sample\ gas}}\right).$$

The present invention also involves an apparatus known as a volumetric flow corrector for measuring a correction factor to adjust a flowrate $Q_f$ of a pipeline gas flowing through a pipeline to a pipeline gas base condition volumetric flowrate $Q_b$. The volumetric flow corrector works in conjunction with a pipeline gas meter which responds to density and the effects of density in a characteristic manner, and which measures the flowrate $Q_f$ of the pipeline gas flowing through the pipeline. The volumetric flow corrector has a conduit for flowing sample gas from the pipeline; a sample gas flowmeter for measuring a flowrate $Q_f'$ of the sample gas through the conduit; a sample gas energy flowmeter for measuring a base condition energy flowrate $E_{sample\ gas}$ (energy per unit time) of the sample gas flowing through the conduit; and a sample gas heating value meter for measuring a base condition heating value $H_{sample\ gas}$ (energy per unit volume) of the sample gas flowing through the conduit. The sample gas flowmeter responds to density and the effects of density in the same manner as the pipeline gas meter. The sample gas in the sample gas flowmeter is maintained at substantially the same temperature as a pipeline gas in the pipeline. A control system receives a signal representing the flowrate $Q_f'$ of the sample gas from the sample gas flowmeter, a signal representing the base condition energy flowrate $E_{sample\ gas}$ of the sample gas from the sample gas energy flowmeter, and a signal representing the base condition heating value $H_{sample\ gas}$ of the sample gas from the sample gas heating value meter. The control system then determines the correction factor from this information.

The volumetric flow corrector can also have a mass flow splitter for splitting the flow of sample gas through the conduit into a test and waste stream after the sample gas flowmeter measures the sample gas flowrate $Q_f'$ through the conduit.

Preferably, the volumetric flow corrector uses a burner, a temperature sensor and either an air flow adjuster or a sample gas flow adjuster as an energy flowmeter. Also preferably, the sample gas heating value meter uses a burner and a reference gas.

The general object of the present invention is to allow accurate measurement of energy flowrates, volume correction ratios $$\frac{Q_b}{Q_f}$$

and adjusted volumetric flowrates $Q_b$ (i.e., base condition volumetric flowrates) in an improved manner. A particular object of the present invention is to eliminate the need to consider density or supercompressibility when making these measurements.

The present invention improves the accuracy of these measurements because it alleviates the need to consider the effects of supercompressibility, temperature, pressure, density, or composition. It can do this because the critical measurement (i.e., the sample gas volumetric flowrate $Q_f'$) is made when the sample gas is at a condition related to pipeline conditions.

Another advantage of the present invention is that measurement of the base condition sample gas volumetric flow $Q_b'$ is extremely accurate because the relation between the amount of air and the paraffin gas energy content when combusted at maximum flame temperature is accurate within 0.1%.

Yet another advantage of the present invention is that it allows intermittent referencing from a reference gas to ensure that the measurement of the sample gas heating valve $H_{sample\ gas}$ is accurate and does not drift.

Another object of the present invention is to monitor the pipeline gas without substantially disrupting the flow of pipeline gas through the pipeline. The present invention achieves this object by deriving the volume correction ratio $$\frac{Q_b}{Q_f}$$

or other results by tapping sample gas from the pipeline and making measurements on the sample gas at a location isolated from the pipeline.

The foregoing and other objects and advantages of the present invention will appear from the following description. In the description, references are made to the accompanying drawings which form a part hereof and in which preferred embodiments of the present invention is shown by way of illustration. Such embodiments do not necessarily represent the full scope of the invention.

BRIEF DESCRIPTION OF THE DRAWINGS

For a more complete understanding of this invention, a reference should now be had to the embodiments illustrated in greater detail in the accompanying drawings and described below by way of examples of the invention. In the drawings:

FIG. 5 is a schematic drawing showing a preferred embodiment of the present invention which uses a chamber to measure sample gas flowrate;

FIG. 6 is a plot of pressure in the chamber shown in FIG. 5 with respect to time;

FIG. 12 is a schematic drawing showing a preferred capillary tube for use in the embodiment shown in FIG. 10;

FIG. 13 is a schematic drawing showing a cross-section of an obstruction disk shown in FIG. 12;

FIG. 14 is a plot of the discharge coefficient for the capillary tube shown in FIG. 12 with respect to Reynold's Number;

DESCRIPTION OF THE PREFERRED EMBODIMENT

Figure 1:
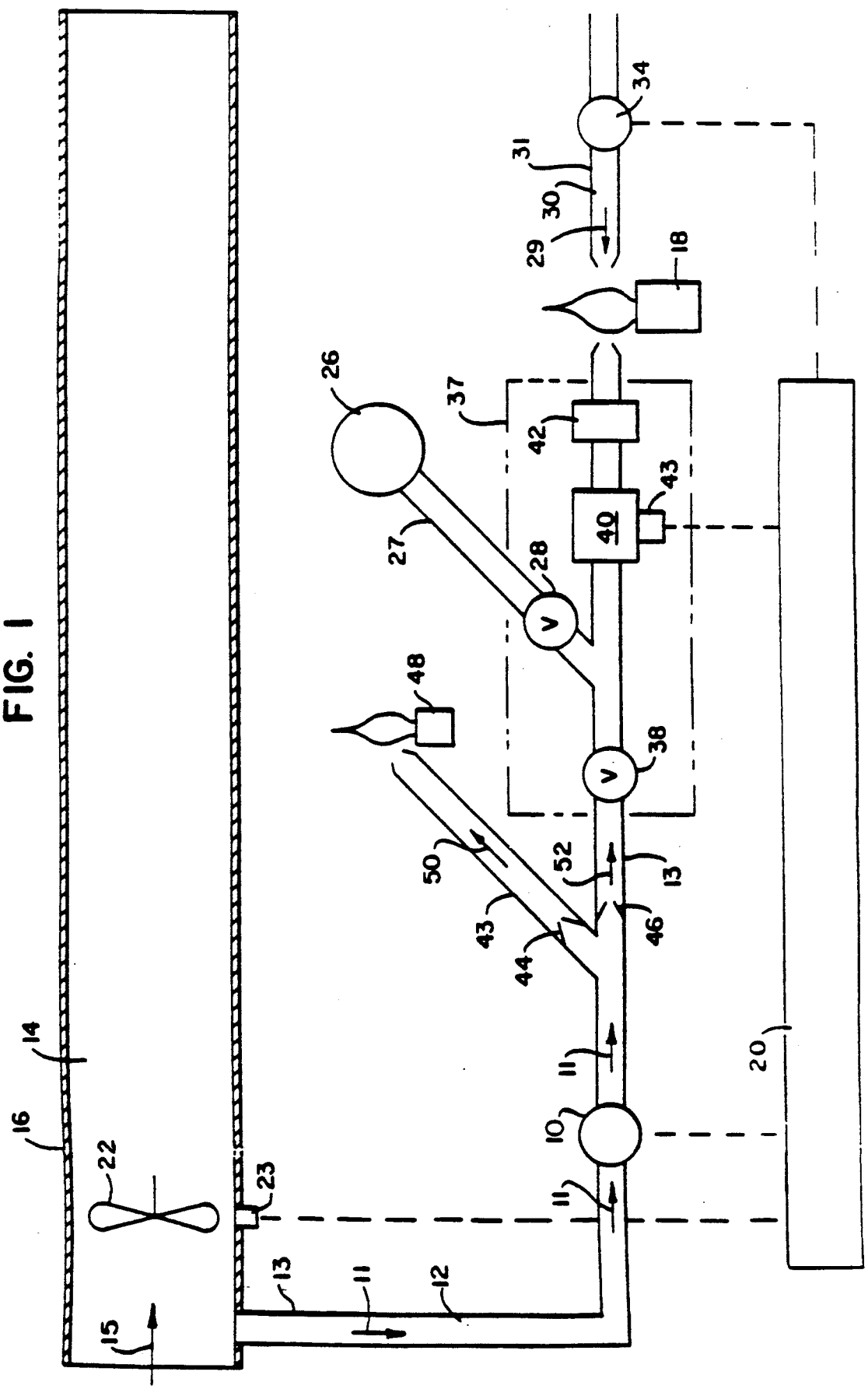
FIG. 1 is a schematic drawing showing apparatus of the present invention.

Referring to FIG. 1, the apparatus of the present invention is used in conjunction with a pipeline gas 22 flowmeter that measures a flowrate $Q_f$ of a pipeline gas 14 flowing through a pipeline 16 in the direction of arrow 15. The measured pipeline gas flowrate $Q_f$ is typically a volumetric flowrate, but it can also take other forms, such as mass flowrate or variations thereof.

The apparatus of the present invention can be thought of generally as a sample gas meter 10 for measuring a flowrate $Q_f'$ of sample gas 12 flowing through a conduit 13 in the direction of arrow 11, where the sample gas 12 is tapped from the flow of pipeline gas 14 through the pipeline 16; a sample gas energy detector 18 for monitoring a sample gas energy flowrate (energy/time) $E_{sample\ gas}$ and for monitoring a sample gas heating value (energy/volume) $H_{sample\ gas}$; and a control system 20 for computing a base condition volumetric flowrate $Q_b$ for the pipeline gas 14 flowing through the pipeline 16. The control system 20 computes the pipeline gas base condition volumetric flowrate $Q_b$ from an electronic signal representing the pipeline gas flowrate $Q_f$ as measured by the pipeline gas flowmeter 22, and generated by a signal generator 23, a signal from the sample gas meter 10 representing the flowrate $Q_f'$ of the sample gas, and signals from a sample gas burner flow adjuster or meter 37 (collectively components 28, 38, 40, 42, and 43) and possibly from an air flowmeter 34 which represent $E_{sample\ gas}$ and $H_{sample\ gas}$.

In addition, the control system 20 can compute the energy flowrate (energy/time) of the pipeline gas 14 through the pipeline 16. The pipeline gas energy flowrate is easily calculated by multiplying the sample gas energy flowrate $E_{sample\ gas}$ by the ratio $$\frac{Q_f}{Q_f'},$$

which is the ratio of the pipeline gas 14 flowrate $Q_f$ as measured by the pipeline gas flowmeter 22 located in the pipeline 16 compared to the sample gas flowrate $Q_f'$ as measured by the sample gas flowmeter 10.

The base condition volumetric flowrate $Q_b$ for the pipeline gas 14 can be derived from the measured flowrate $Q_f$ of the pipeline gas by adjusting $Q_f$ to correspond to what the volumetric flowrate would be at defined base conditions, such as 60° F. and 14.7 psi. The American Gas Association has set standards for both linear and orifice volumetric meters to determine the volume correction ratio $$\frac{Q_b}{Q_f}$$

used to derive an adjusted or base condition volumetric flowrate $Q_b$ from a measured flowrate $Q_f$. The AGA relation may be stated as:

$$\frac{Q_b}{Q_f} = \left( F_{Pf} F_{Pb} F_{Tf} F_{Tb} \frac{Z_b}{Z_f} \right) \quad (2)$$

where $F_{Pf}$ is a pressure factor at flow conditions, $F_{Pb}$ is a pressure factor at base conditions, $F_{Tf}$ is a temperature factor at flow conditions, $F_{Tb}$ is the temperature factor at base conditions, and the ratio $$\frac{Z_b}{Z_f}$$

is the ratio of the compressibility factor at base conditions to the compressibility factor at flow conditions. The present invention alleviates the need to use a relation such as Eq. (2).

In the present invention, the volume correction ratio $$\frac{Q_b}{Q_f}$$

for a pipeline gas 14 flowing through a pipeline 16 is equivalent to a volume correction ratio $$\frac{Q_b'}{Q_f'}$$

for sample gas 12 tapped from the pipeline 16. That is:

$$\frac{Q_b}{Q_f} = \frac{Q_b'}{Q_f'} \quad (3)$$

The relation in Eq. (3) is true if the temperature, pressure, and composition of the gas flowing through the sample gas flowmeter 10 is substantially the same as the temperature, pressure, and composition of the pipeline gas 14 flowing through the pipeline 16. The pressure and the composition of the sample gas 12 are substantially the same as the pressure and the composition of the pipeline gas 14 flowing through the pipeline 16 because the sample gas 12 flowing to the sample gas flowmeter 10 is tapped directly from the pipeline 16.

Figure 2:
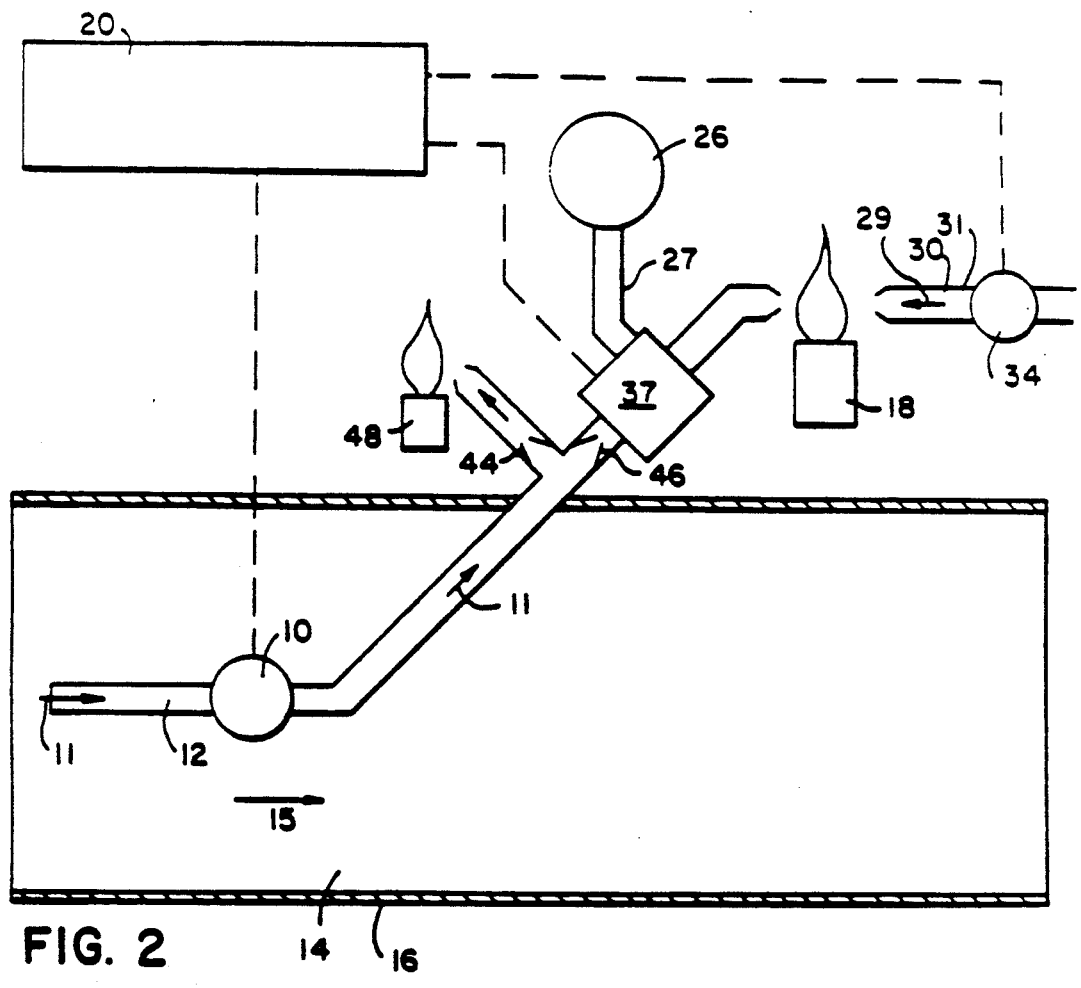
FIG. 2 is a schematic drawing showing a sample gas flowmeter residing within a pipeline gas flow in a pipeline.

Referring to FIG. 2, the temperature of the sample gas 12 can be maintained at substantially the same temperature as the pipeline gas 14 by immersing the sample gas flowmeter 10 into the stream of pipeline gas 14 flowing through the pipeline 16. Alternatively, referring to FIG. 3, the sample gas 12 can be maintained at substantially the same temperature as the pipeline gas 14 flowing through the pipeline 16 by routing the sample gas 12 to a sample gas flowmeter 10 through a longer serpentined conduit 24 where both the serpentined conduit 24 and the sample gas flowmeter 10 are mounted in intimate contact with the outside surface of the pipeline 16. Insulation 25 should be placed around the serpentined conduit 24, the sample gas flowmeter 10 and the pipeline 16 to facilitate temperature equalization.

Figure 3:
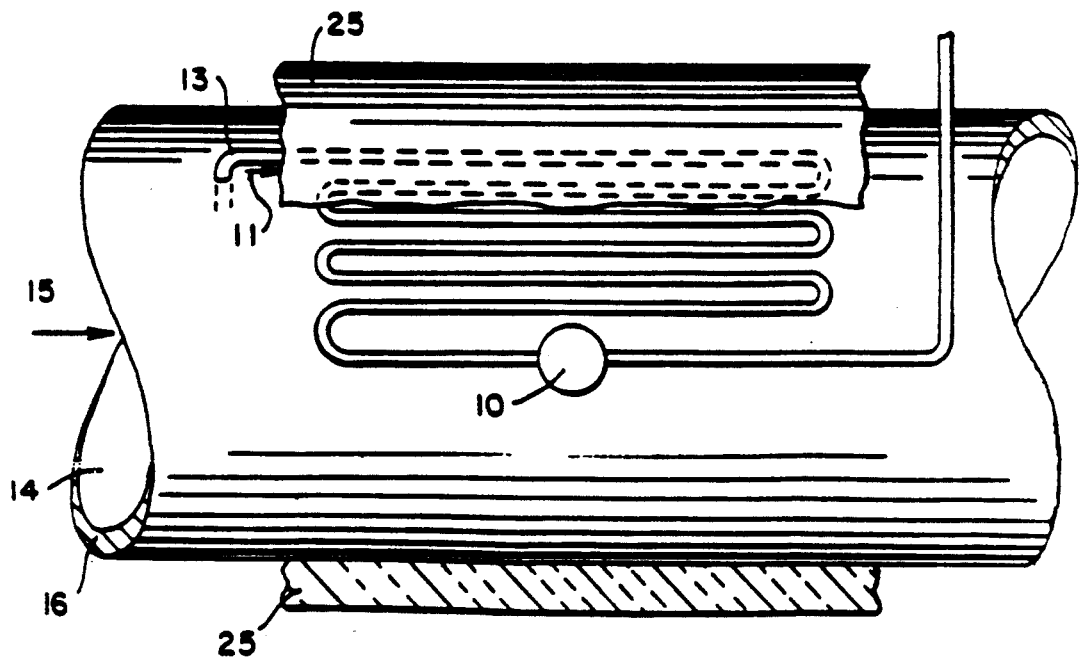
FIG. 3 is a schematic drawing showing a sample gas flowmeter being mounted in intimate contact with a pipeline.

With either the configuration shown in FIG. 2 or the configuration shown in FIG. 3, the temperature of the sample gas 12 within the sample gas flowmeter 10 can be maintained at substantially the same temperature as the temperature of the pipeline gas 14 flowing through the pipeline 16. Under these conditions, Eq. (3) applies and the volume correction ratio for the sample gas $$\frac{Q_b'}{Q_f'}$$

can be measured and used to adjust the pipeline gas 14 flowrate $Q_f$ as measured by the pipeline gas flowmeter 22 to derive the pipeline gas base condition volumetric flowrate $Q_b$ as shown by the following relation:

$$Q_b = Q_f \left( \frac{Q_b'}{Q_f'} \right) \quad (4a)$$

or upon rearranging:

$$Q_b = Q_{b'}\left(\frac{Q_f}{Q_{f'}}\right) \tag{4b}$$

Referring to Eq. (4b), a goal of this invention is to measure the pipeline gas base condition volumetric flowrate $Q_b$ without considering the effects of density. The sample gas base condition volumetric flowrate $Q_{b'}$ is measured using energy methods and can be done without considering density. On the other hand, the ratio $$\left(\frac{Q_f}{Q_{f'}}\right)$$

can be measured without considering density only if the sample gas flowmeter 10 responds to the density of sample gas 12 whose flowrate is being measured by the sample gas flowmeter 10 in a manner similar to the way the pipeline gas flowmeter 22 responds. If flowmeters 10 and 22 do not respond to density in a symmetric manner, the effects of density will not cancel each other. Therefore, the sample gas flowmeter 10 should respond to density in the same manner as the pipeline gas flowmeter 22 to enable the elimination density considerations from the measurement of the pipeline gas base condition volumetric flowrate $Q_b$.

Determination Of The Sample Gas Base Condition Volumetric Flow $Q_{b'}$

Referring generally to FIG. 1, the sample gas base condition volumetric flowrate $Q_{b'}$ is measured by energy methods as described by the following relation:

$$Q_{b'} = \frac{E_{sample\ gas}}{H_{sample\ gas}} \tag{5}$$

where $E_{sample\ gas}$ is the base condition energy flowrate of the sample gas 12 through the sample gas flowmeter 10 (energy/time) and $H_{sample\ gas}$ is the base condition heating value of the sample gas 12 flowing through the sample gas flowmeter 10 (energy/volume). The base condition energy flowrate $E_{sample\ gas}$ and the heating value $H_{sample\ gas}$ of the sample gas 10 are determined by flowing the sample gas 12 to the burner 18 and burning the sample gas 12 with air 30 which is also flowed to the burner 18 in the direction of arrow 29.

Reference can be made to U.S. Pat. Nos. 3,777,562; 4,062,236; 4,125,018; and 4,125,123, all issued to Clingman, which describe how the heating value and the energy content of the sample gas 12 can be measured. In brief, the amount of air 30 required to completely combust a saturated hydrocarbon gas (e.g., sample gas 12 flowing to the burner 18) at a maximum flame temperature is proportional to the energy released during combustion. In fact, the energy flowrate of a saturated hydrocarbon gas is related to the air 30 flowrate $\Omega_{air}$ through a constant $K_{max}$ which has a known and constant value for all saturated hydrocarbon gases, with or without inert fractions. If inert gases are mixed with the fuel, the temperature of the flame reduces due to inert cooling, however, at the maximum temperature for the fuel mixture, the relation between the heating value and the fuel-air ratio remains absolute. Also, $K_{max}$ remains accurate even with mixtures of gas containing small fractions of non-paraffinic gases such as hydrogen.

Figure 4A:
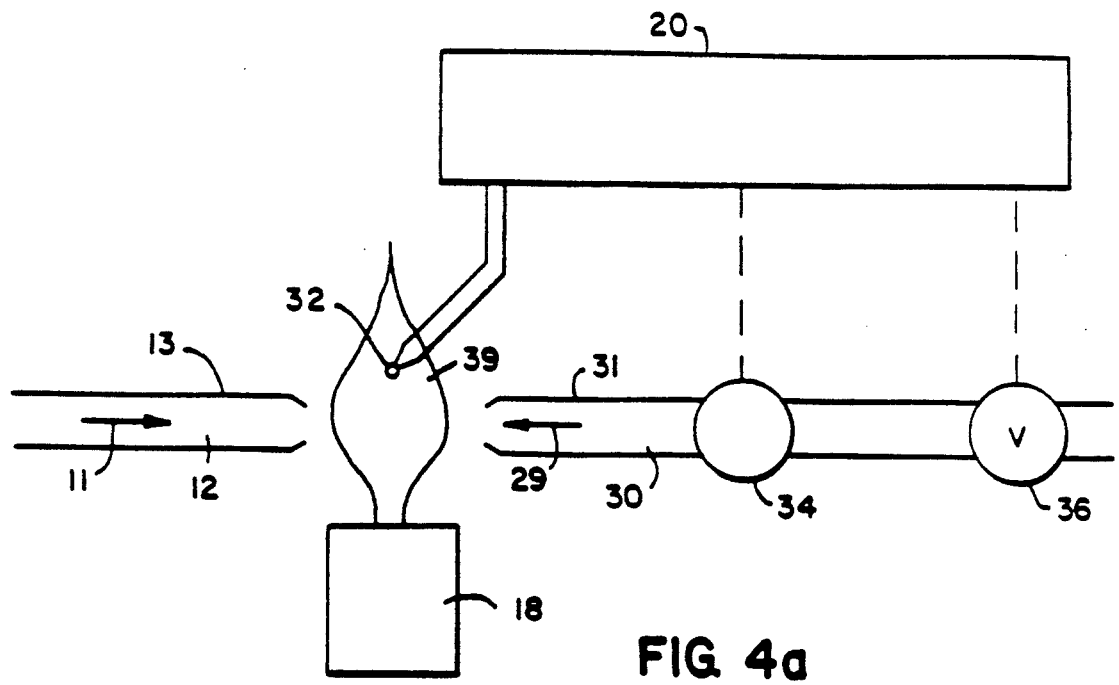
FIGS. 4a and 4b are schematic drawings showing apparatus for measuring the energy flowrate and heating value of the sample gas.

Using this stoichiometric method, the base condition energy flowrate $E_{burner}$ of the sample gas 12 flowing to the burner 18 can be represented by:

$$E_{burner} = K_{max}\Omega_{air} \tag{6}$$

where $K_{max}$ is the stoichiometric proportionality constant, and $\Omega_{air}$ is the air mass flowrate to the burner 18. Referring in particular to FIG. 4a, sample gas 12 flows to the burner 18 after it flows from the sample gas flowmeter 10 and possibly other apparatus which is described below. Air 30 is supplied to the burner 18 in the direction of arrow 29 through an air hose 31. The sample gas 12 burns with the air 30 above the burner 18 to form a flame 37. A thermocouple 32 monitors the flame 39 temperature and communicates to the control system 20. Air 30 flowing through the air hose 31 is monitored by an air mass flowmeter 34. Air mass flowmeters are old in the art and are accurate in ambient conditions. The air flow 30 is adjusted by an air valve 36, which is controlled by the control system 20, until the sample gas 12 burns at maximum flame temperature. When the flame burns at the maximum flame temperature, the base condition sample gas energy flowrate $E_{sample\ gas}$ can be determined from a signal from the air flowmeter 34 using Eq. (6).

While an air mass flowmeter 34 is the preferred way of measuring the air mass flowrate $\Omega_{air}$, a volumetric or a molar flowmeter can be used. Note, also, that the base condition sample gas energy flowrate $E_{sample\ gas}$ can be measured by flowing a constant air mass flowrate $\Omega_{air}$ to the burner 18 and adjusting a flowrate $Q'_{burner}$ of sample gas 12 to the burner 18 until maximum flame temperature is achieved. When maximum flame temperature is achieved, the base condition energy flowrate $E_{burner}$ of sample gas 12 to the burner 18 can again be determined from Eq. (6).

Figure 4B:
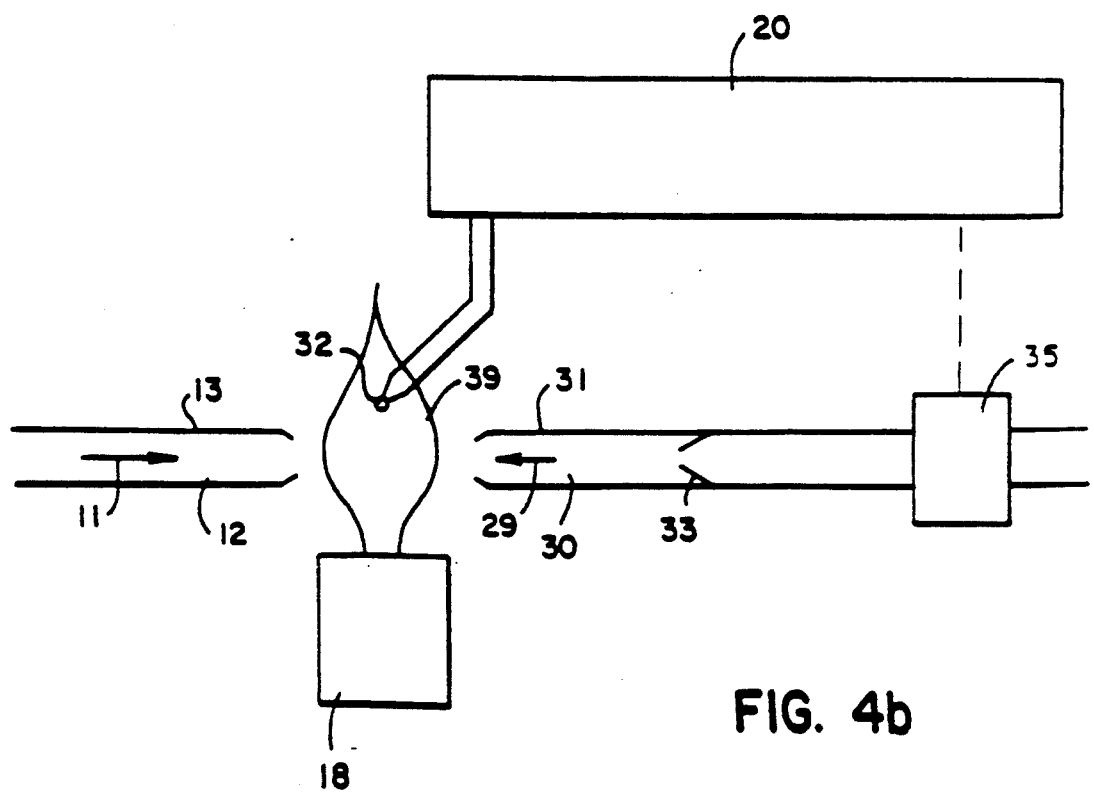

One way to flow air to the burner 18 at a constant flowrate is to flow air through a sonic nozzle under critical flow conditions. Referring to FIG. 4b, such an air system is composed of a very accurate pressure controller 35 forcing air into a sonic nozzle 33. The resulting air flow 30 burns with sample gas 12 in the burner 18. It is preferred that the pressure controller 35 communicate with the control system 20 so the air flowrate $\Omega_{air}$ be known in the control system 20. The use of the sonic nozzle 33 under critical flow conditions results in long-term air flow stability. The number of oxygen molecules forced to combustion is very stable. The air flow 30 through the sonic nozzle 33, assuming critical pressure is exceeded, is described as:

$$\omega_{air} = \frac{K_{air}P_{air}}{T_{air}} \tag{7}$$

where $K_{air}$ is the nozzle 33 constant for air, $P_{air}$ is absolute pressure at the nozzle 33 inlet and $T_{air}$ is the absolute temperature at the nozzle 33 inlet. If air pressure $P_{air}$ is maintained constant, the air flow 30 to the burner 18 is constant, and the sample gas energy flowrate to the burner 18 ($E_{burner}$) can remain constant by adjusting the flowrate ($Q'_{burner}$) of sample gas 12 to the burner 18. Referring to FIG. 1, the sample gas 12 flowrate $Q'_{burner}$ to the burner 18 can be measured using a solenoid valve 38, a volume chamber 40, and a flow controller 42 in the conduit 13 as the sample gas 12 flows to the burner 18. Such a volumetric or molar flowmeter for measuring the flowrate $Q'_{burner}$ of sample gas 12 to the burner 18 is described in U.S. Pat. No. 4,285,245, issued Aug. 25, 1981, by Kennedy. This is the preferred way to adjust and measure $Q'_{burner}$, but other ways are known in the art and are acceptable.

A reference gas 26 with a known heating value at base conditions $H_{reference\ gas}$ is used to determine the base condition heating value of the sample gas $H_{sample\ gas}$. Methane is a suitable reference gas 26. At U.S. base conditions of 60° F. and 14.7 psi, methane has a heating value of about 1,014 Btu/standard cubic foot. In general, the base condition sample gas heating value $H_{sample\ gas}$ can be determined by intermittently flowing the reference gas 26 to the burner 18 and measuring flowrate. Using a reference gas 26 allows the base condition sample gas heating value $H_{sample\ gas}$ to be determined without measuring ambient temperature and pressure.

The energy flowrate of the sample gas flowing to the burner can be represented as the sample gas heating value $H_{sample\ gas}$ (energy per unit volume) multiplied by the sample gas volumetric flowrate to the burner $Q_{sample\ gas}$ (volume/time). Likewise, the energy flowrate of the reference gas flowing to the burner can be represented as the reference gas heating value $H_{reference\ gas}$ multiplied by the reference gas volumetric flowrate to the burner $Q_{reference\ gas}$. Also, from Eq. (6), it can be seen that the ratio of the energy flowrate of the sample gas flowing to the burner compared to the energy flowrate of the reference gas flowing to the burner is the ratio $$\frac{\omega_{air\ sample}}{\omega_{air\ reference}}$$

where $\Omega_{air\ sample}$ is the air flowrate to the burner when the sample gas is being burned at maximum flame temperature, and $\omega_{air\ reference}$ in the air flowrate to the burner when the reference gas is being burned at maximum flame temperature. The base condition sample gas heating value $H_{sample\ gas}$ can therefore be generally represented by:

$$H_{sample\ gas} = H_{reference\ gas} \left( \frac{Q_{reference\ gas}}{Q_{sample\ gas}} \right) \left( \frac{\omega_{air\ sample}}{\omega_{air\ reference}} \right) \quad (8)$$

Referring still to FIG. 1, a reference gas 26 can be hooked-up via line 27 and valve 28 to use volume 40 and flow controller 42 for measuring the flowrate of a reference gas 26 flowing to the burner 18. As is described in U.S. Pat. No. 4,285,245, flowrate can be measured by determining the rate of pressure decay in chamber 40. For instance, to measure the flowrate $Q_{sample\ gas}$ of the sample gas 12 flowing to the burner 18, valve 28 is closed, and valve 38 is opened, and volume 40 is allowed to fill with sample gas 12. Valve 38 is then closed and the time rate of change of pressure in volume 40 is determined as the sample gas 12 within volume 40 flows through the flow controller 42 to the burner 18. To measure the flowrate $Q_{reference\ gas}$ of reference gas 26 flowing to the burner 18, valve 38 is closed and valve 28 is open so that the chamber 40 can fill with reference gas 26. Then valve 28 is closed and the time rate of change of pressure in volume 40 is measured as reference gas 26 flows to the burner 18.

Assuming that the air flow $\omega_{air}$ to the burner is constant between referencing and sampling periods, the sample gas heating value at base conditions (energy per unit volume) $H_{sample\ gas}$ can be determined from the following relation:

$$H_{sample\ gas} = \frac{\frac{\partial P}{\partial t}\bigg|_{reference\ gas}}{\frac{\partial P}{\partial t}\bigg|_{sample\ gas}} H_{reference\ gas} \quad (9)$$

where $$\frac{\partial P}{\partial t}$$

is the time rate of change of pressure in chamber 40 and $H_{reference\ gas}$ is the heating value at base conditions for the reference gas 26.

The following analysis explains the determination of $$\frac{\partial P}{\partial t}$$

in Eq. (9). The rate of pressure change in the chamber 40 with a constant molar flowrate therefrom (or controlled by flow controller 42) is:

$$\frac{\partial P}{\partial t} \left( \frac{V}{RT} \right) = Z \frac{\partial n}{\partial t} + n \frac{\partial Z}{\partial t} \quad (10)$$

where V is the volume of chamber 40, T is the temperature of gas in the chamber 40, R is a universal gas constant, n is the amount of moles of gas in the chamber 40, $$\frac{\partial n}{\partial t}$$

is the time rate of change of the amount of moles in the chamber 40, Z is the supercompressibility factor for the gas in the chamber 40 and $$\frac{\partial Z}{\partial t}$$

is the time rate of change of Z as the gas flows from chamber 40. The time rate of change of Z can be expressed as:

$$\frac{\partial Z}{\partial t} = \frac{\partial P}{\partial t} \left( \frac{\partial Z}{\partial P} \right)_T \quad (11)$$

where $$\left( \frac{\partial Z}{\partial P} \right)_T$$

is the rate of change of Z with respect to pressure at constant temperature.

Substituting Eq. (10) into Eq. (11) and simplifying gives:

$$\frac{\partial P}{\partial t}\left(\frac{V}{RT}\right)\left[Z - P\left(\frac{\partial Z}{\partial P}\right)_T\right] = Z^2 \frac{\partial n}{\partial t} \quad (12)$$

The supercompressibility of the gas Z can be written as a virial power series with pressure coefficients that are a function of temperature and composition only:

$$Z = 1 + b(T,x)P_m + c(T,x)P_m^2 + \ldots \quad (13)$$

where $P_m$ is the pressure at which Z is being computed and b(T,x) and c(t,x) are the second and third virial coefficients. Higher order terms can be neglected because of the relatively low pressures in chamber 40. Substituting Z and $$\left(\frac{\partial Z}{\partial P}\right)$$

into Eq. (13) and simplifying gives:

$$\frac{\partial P_m}{\partial t}\left(\frac{V_m}{RT}\right) = [1 + 2bP_m + (3c + b^2)P_m^2]\frac{\partial n}{\partial t} \quad (14)$$

Equation (14) shows that $$\frac{\partial P}{\partial t}$$

measurements are independent of molecular weight. Therefore, the heating value in Eq. (9) can be measured independent of molecular weight changes which could be due to composition changes. Substituting Eq. (14) into Eq. (9) gives the relation:

$$H_{sample\ gas} = \frac{\left(TZ'\frac{\partial n}{\partial t}\right)_{reference\ gas}}{\left(TZ'\frac{\partial n}{\partial t}\right)_{sample\ gas}} H_{reference\ gas} \quad (15)$$

where Z' represents $[1+2bP_m+(3c+b^2)P_m^2]$. To solve for $H_{sample\ gas}$ in Eq. (15), the temperature of the sample gas 12 must be compared to the temperature of the reference gas 26 at the time of referencing. The temperature of the sample gas 12 is not compared to the base condition temperature.

Also, to solve for $H_{sample\ gas}$ in Eq. (15), the Z' ratio of the sample gas 12 compared to the reference gas 26 must be determined. It is necessary to consider only the first and second terms in the Z' expansion because relatively low pressures in chamber 40 make higher terms negligible. Eq. (15) then becomes:

$$H_{sample\ gas} = \frac{\left(T(1 + 2bP_m)\frac{\partial n}{\partial t}\right)_{reference\ gas}}{\left(T(1 + 2bP_m)\frac{\partial n}{\partial t}\right)_{sample\ gas}} H_{reference\ gas} \quad (16)$$

Equation (16) includes two "2bP" terms—one at the sample gas 12 conditions and one at the reference gas 26 conditions. The pressure $P_m$ at which the rate of change of pressure in chamber 40 is measured remains constant whether measuring sample gas 12 flowrate or reference gas 26 flowrate, so Eq. (16) can be reduced to:

$$H_{sample\ gas} = \frac{\left(T\frac{\partial n}{\partial t}\right)_{reference\ gas}}{\left(T\frac{\partial n}{\partial t}\right)_{sample\ gas}} (1 + 2(b_{sam} - b_{ref})P_m) H_{reference\ gas} \quad (17)$$

The importance of Eq. (17) is that the sample gas 12 heating value at base conditions $H_{sample\ gas}$ can be determined from the reference gas 26 heating value at base conditions $H_{reference\ gas}$ using Eq. (9), without any need to monitor temperature and pressure at the time the measurements are made. This is because 1) the ratio $$\frac{\left(\frac{dP}{dt}\right)_{reference\ gas}}{\left(\frac{dP}{dt}\right)_{sample\ gas}}$$

in Eq. (9) is inherently determined for the flow temperature of the reference gas 26, not for the standard temperature (e.g. 60° F.); and 2) the pressure in chamber 40 at which $$\left(\frac{dP}{dt}\right)_{sample\ gas} \text{ and } \left(\frac{dP}{dt}\right)_{reference\ gas}$$

are measured can be held constant. Therefore, $H_{sample\ gas}$ can be determined from $H_{reference\ gas}$ regardless of the ambient conditions.

It is important to note that the above derivation for the sample gas 12 heating value $H_{sample\ gas}$ is made with one major assumption—that the air flow $\omega_{air}$ to the burner 18 (where maximum flame temperature is achieved) is absolutely constant between referencing and sampling periods. If the air flow were to change, Eq. (9) must be modified to $$H_{sample\ gas} = \frac{\frac{dP}{dt}_{reference\ gas}}{\frac{dP}{dt}_{sample\ gas}} \left(\frac{\omega_{air\ sample}}{\omega_{air\ reference}}\right) H_{reference\ gas} \quad (18)$$

Equation (18) shows that air flow to the burner 18 can be adjusted in lieu of adjusting gas flowrate or along with adjusting gas flowrate.

Measurement Of The Sample Gas Flowrate $Q_f'$

As noted above, the sample gas flowmeter 10 should respond to density in the same manner as the pipeline gas flowmeter 22 in order to eliminate density considerations from the measurement of the pipeline gas base condition volumetric flowrate $Q_b$. A more detailed explanation of this concept now follows. The relationship between the sample gas flowmeter 10 response signal X' and the measured sample gas volumetric flowrate $Q_f'$ is given by the following relation:

$$Q_f' = K_f f(\rho')X' \quad (19)$$

where $X'$ is the sample gas flowmeter 10 response signal that is generated by the sample gas flowmeter 10 in response to the sample gas volumetric flowrate $Q'_f$, $K_f'$ is a scaling coefficient that may vary slowly with Reynold's Number (but for the purposes of this invention, can be considered to be constant with change in density), $\rho'$ is the density of the sample gas 12, and $f'(\rho')$ is a density function associated with the sample gas flowmeter 10. In a similar manner, the relationship between the pipeline gas flowmeter 22 response signal $X$ and the measured pipeline gas volumetric flowrate $Q_f$ is given by:

$$Q_f = K_f f(\rho) X \qquad (20)$$

where the unprimed symbols refer to the pipeline gas flowmeter 22 and the term definitions are otherwise consistent with Eq. (19). Substituting Eqs. (19) and (20) into Eq. (4b) gives:

$$Q_b = Q_{b'} \left( \frac{K_f f(\rho) X}{K_f' f(\rho') X'} \right) \qquad (21)$$

where, as described above, the sample gas base condition volumetric flowrate $Q_{b'}$ is measured by energy methods and can be measured without considering density. The scaling coefficients $K_f$ and $K_f'$ are essentially constant with density, at least over the range in which the flowmeter 22 and 10 are expected to operate, so the ratio $$\frac{K_f}{K_f'}$$

can be considered to be constant and independent of density. Also, the density $\rho$ of the pipeline gas 14 is substantially the same as the density $\rho'$ of the sample gas 12 because the temperature, pressure, and composition of the sample gas 12 is substantially the same as the pipeline gas 14. Therefore, if the sample gas flowmeter 10 density function $f'(\rho')|_{\rho'=\rho}$ and the pipeline gas meter 22 density function $f(\rho)$ are homogeneous, the measurement of the pipeline gas base condition volumetric flowrate $Q_b$ can be made without considering the effect of density. For example, the need to consider the effect of density can be alleviated by matching a linear sample gas flowmeter 10 with a linear pipeline gas flowmeter 22, or a differential pressure sample gas flowmeter 10 with a differential pressure pipeline gas flowmeter 22, or a sample gas mass flowmeter 10 with a pipeline gas mass flowmeter 22, etc.

Turbine meters, vortex meters, diaphragm meters, positive displacement meters as well as other types of meters are linear flowmeters. The response signal $X$ (or $X'$) for a linear flowmeter is typicality a frequency (but, can be any of a number of responses such as signal time rate of change of pressure.) The volumetric flowrate given by a linear flowmeter is independent of density so the density function $f(\rho) = 1$. For a typical mass flowmeter (such as a thermal meter or coriolis meter), the response signal can be a temperature difference or some other indicia of mass flow; so the density function $f(\rho) = \rho$. For a differential pressure meter (such as an orifice or a venturi), the response is typically the square root of a pressure drop (i.e., $X = \sqrt{\Delta P}$); and, the volumetric flowrate depends on the square root of the specific gravity of the gas (i.e., $f(\rho) = \sqrt{1/\rho}$). To alleviate the need to consider density when measuring $Q_b$, the sample gas flowmeter 10 density function $f'(\rho')|_{\rho'=\rho}$ must match the pipeline gas flowmeter 22 density function $f(\rho)$.

Sample gas 12 flowrates expected to flow to the burner 18 are relatively small, generally about one standard cubic foot per hour, or about 0.05 pounds per hour. Usual flowmeter structures such as turbine, vortex, and other types of meters do not consistently accomplish accurate measurements at this small flowrate. Disclosed later in this discussion are two flowmeters which can produce accurate measurements at small flow conditions. Before discussing these two sample gas flowmeter 10 arrangements, I will discuss other types of flowmeter arrangements that would be suitable for the sample gas flowmeter 10.

For turbine or vortex sample gas flowmeters, the sample gas 12 flowrate can be represented by $Q'_f = K'_f f'_f$ where $f'_f$ is a frequency and $K'_f$ is a scaling constant. The volume correction ratio $$\frac{Q_{b'}}{Q_f'}$$

is then:

$$\frac{Q_{b'}}{Q_f'} = \frac{E_{sample\ gas}}{K_f' f_f' H_{sample\ gas}} \qquad (22)$$

Small turbine, vortex, or coriolis (if a pipeline gas mass flowmeter is used) flowmeters could operate inside a structure such as shown in FIGS. 2 or 3. But, at present, the inventor does not know of a practical way of fabricating such small turbine, vortex or coriolis meters. In addition to the problems associated with fabricating small turbine, vortex, or coriolis flowmeters, operation of these flowmeters at such low Reynold's Numbers may be problematic. At present, these meters operate properly only at sufficiently high Reynold's Number. Not much is known about the performance of flowmeters in small structures.

One way to overcome the difficulties associated with a small sample gas 12 flow is to operate the sample gas flowmeter 10 at higher flowrates. This would result in excessive sample gas 12 flows well beyond that used in the burner 18. However, as shown in FIG. 1, the sample gas 12 stream can be split using parallel sonic nozzles 44 and 46 after the sample gas 12 flows from the sample gas flowmeter 10. In such a system, sonic nozzle 44 is located in line 43 and sonic nozzle 46 is located in line 13 leading to the burner 18. In FIG. 1, line 43 leads to a catalytic burner 48, but line 43 could lead to another waste method.

Since the temperature, pressure, differential pressure, and composition of the sample gas 12 flowing to the sonic nozzles 44 and 46 is the same, the volumetric flow of sample gas 12 flowing from the sample gas flowmeter 10 can be split in a known ratio into a waste stream 50 flowing through line 43 and a test stream 52 flowing to the burner 18 and associated apparatus. The sonic nozzles 44 and 46 can generally be thought of as a flow splitter.

Another way to overcome the consequences of non-linearities in flowmeter response to fluid flow is to hold the sample gas flowrate $Q_f'$ constant (or at least at a constant Reynold's Number). This would allow operation in a non-linear region of a flowmeter performance curve without sacrificing overall accuracy.

Presently, I know of two sample gas flowmeter 10 systems that can accurately measure the sample gas flowrate $Q_f$ at low flow rates. One system uses a fixed volume chamber and operates with a linear pipeline gas flowmeter. The other uses a capillary tube and operates with a differential pressure pipeline gas flowmeter. These systems are discussed below in seriatim.

Method and Apparatus for Measuring $Q_f$ With a Chamber of Fixed-Volume

This system for measuring the sample gas 12 flowrate $Q_f$ would typically be used with a pipeline gas volumetric flowmeter 22 of the type considered to be a linear flowmeter (i.e., a flowmeter that produces a signal directly proportional to flow velocity). The apparatus and method of this system are depicted in FIGS. 5–8.

In FIG. 5, the sample gas flowmeter shown generally as 10 is used in conjunction with a turbine meter 110. The turbine meter 110 measures the volumetric flowrate $Q_f$ of a pipeline gas 14 flowing through the pipeline 16 in the direction of arrow 15. The turbine meter 110 communicates the volumetric flowrate $Q_f$ of the pipeline gas 14 as the ratio of turbine frequency $f_t$ compared to a turbine meter factor $K_t$. The turbine meter factor $K_t$ is normally stored in the control system 20; whereas, the turbine frequency $f_t$ is relayed to the control system 20 periodically.

In this embodiment, the control system 20 is an electrical system utilizing conventional switching techniques to operate the instrumentation in accordance with the procedures of the invention. If desired, the control system 20 may employ conventional solid state microprocessor techniques, such as: an electronic timing device or clock, an analog-to-digital converter, output signal amplifiers, storage memory for the control program, an arithmetic unit for dividing, and the like.

A sample of gas 12 is tapped upstream of the flowmeter 110 at point 119. The sample gas 12 flows into a first fixed-volume chamber 120. The volume of the chamber is small, about 20 cubic centimeters. The sample gas 12 must be maintained at substantially the same temperature as the pipeline gas 14 when it is in the first chamber 120. If the temperature of the sample gas 12 is maintained at substantially the same temperature as the pipeline gas 14, the need to compensate for the effects of supercompressibility can be avoided.

The flow of sample gas 12 into the first chamber 120 is controlled by a first solenoid valve 122. Referring to FIG. 6, the first solenoid valve 122 is open at the beginning of a sampling cycle 124 and sample gas 12 flows into the first chamber 120. When the pressure in the first chamber 120 reaches a pressure $P_L$ of the pipeline gas 14 in the pipeline 16, the first solenoid valve 122 closes and terminates the flow of sample gas 12 into the first chamber 120. The sample gas 12 may be held within the first chamber 120 at the pipeline pressure $P_L$ to assure that the sample gas 12 is substantially the same temperature and density as the pipeline gas 14.

Referring again to FIG. 5, a flow controller 126 for maintaining a selected flow of sample gas 12 from the first chamber 120 is located downstream of the first chamber 120. Flow controllers are known in the art and an electronically adjustable pressure regulator, or I/P converter 128, followed by a capillary tube 130 is suitable for this application. The I/P converter 128 precisely determines the sample gas 12 pressure in response to an electrical signal 132 from the control system 20 (typically ranging from 4 to 20 ma direct current), and thus determines the flowrate of sample gas 12 through the capillary tube 130.

Referring again to FIG. 6, the flow controller 126 allows sample gas 12 to flow from the first chamber 120 at a selected rate. As the sample gas 12 flows from the first chamber 120 after the first solenoid valve 122 closes, the pressure within the first chamber 120 drops. When the chamber pressure reaches a starting pressure $P_1$, a timer 134 (see FIG. 5) starts. When the pressure in the first chamber 120 drops to a stopping pressure $P_2$, the timer 134 is stopped and the time interval $t_m$ is recorded. The chamber 120 pressure continues to drop until it reaches an opening pressure $P_o$ at which time the first solenoid valve 122 opens and a new sampling cycle 124 begins. This type of apparatus is similar to the invention disclosed in U.S. Pat. No. 4,285,245 issued to Kennedy on Aug. 25, 1981.

Referring again to FIG. 5, a pressure sensor 136 senses the pressure within the first chamber 120. Preferably, the pressure sensor 136 is a strain gauge type sensor with an electrical output, i.e., a pressure transducer, but other types of pressure sensors or transducers may be used if desired.

The pressure sensor 136 communicates with the first solenoid valve 122 and with the timer 134, preferably through the control system 20. When the pressure sensor 136 senses that the pressure in the first chamber has reached the pipeline pressure $P_L$, it communicates to close the first solenoid valve 122. When the sensor 136 senses that the pressure in the first chamber 120 has dropped below the starting pressure $P_1$, it communicates to the timer 134 to begin timing. Likewise, the sensor communicates with the timer 134 to stop timing when the pressure in the first chamber 120 drops below the stopping pressure $P_2$. The sensor 136 also communicates with the first solenoid valve 122 to open the valve 122 when the pressure in the first chamber 120 reaches the opening pressure $P_o$.

Although it is not necessary in all applications, a pressure regulator 138 may be installed in line between the first chamber 120 and the flow controller 126. A pressure regulator 138 may be necessary, for example, when the pipeline gas 14 pressure $P_L$ is high.

In order for the accuracy of the present invention to be substantially independent of the supercompressibility of the pipeline gas 14 two conditions must exist within the first chamber 120:

1) The temperature and pressure of the sample gas 12 within the first chamber 120, at the time the first solenoid valve 122 is closed, must be substantially equal to the temperature and pressure of the pipeline gas 14 in the pipeline 16; and 2) The measurement pressure $P_m$, which is the average of the starting pressure $P_1$ and the stopping pressure $P_2$ should be about one-half of the pressure $P_L$ of the pipeline gas 14 in the pipeline 16. Further, the value of $(P_1 - P_2)$ should be about 10% of $P_L$ or less.

Figure 7:
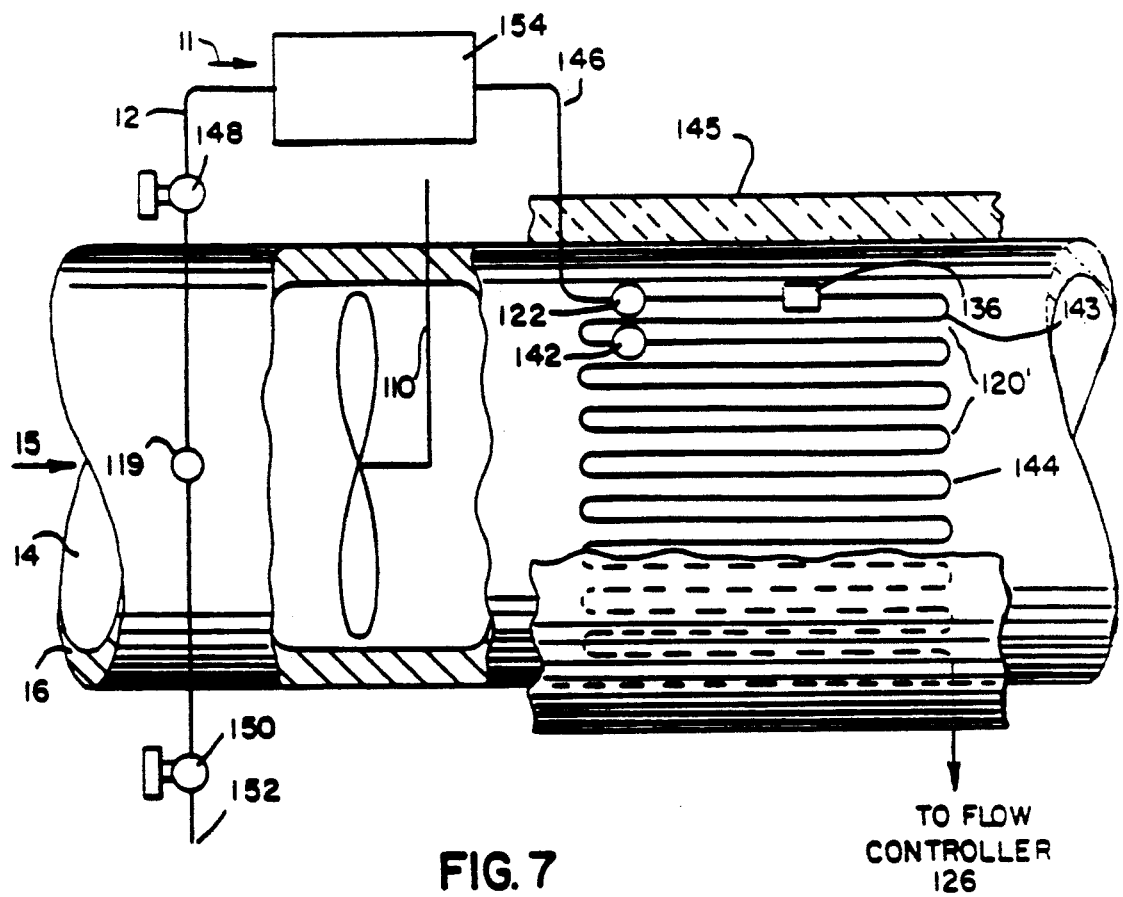
FIG. 7 is a schematic drawing showing the preferred way of mounting the embodiment shown in FIG. 5.

FIG. 7 depicts the use of a serpentined hollow coil 120' as the first fixed-volume chamber 120 to facilitate the occurrence of the two conditions stated above. Referring to FIG. 7, the serpentined hollow coil 120' is located immediately downstream of the first solenoid valve 122. A second solenoid valve 142 is located downstream in the serpentined hollow coil 120'. The volume within the hollow coil 120' that is enclosed by the solenoid valves 122 and 142 is a first section 143 of the first chamber 120. The volume within the hollow coil 120' after the second solenoid 142 and before the flow controller 126 is a second section 144 of the first chamber 120'. The sample gas 12 flows from the second section 144 continuously at a rate selected by the flow controller 126.

The hollow coil 120' is mounted in intimate contact with the pipeline 16 and serpentines back and forth across the outer surface of a portion of the pipeline 16. Insulation 145 should be placed around the hollow coil 120', the solenoid valves 122 and 142, and the pipeline 16. A heat transfer compound may also be used to facilitate temperature equalization. With this configuration, the temperature of the sample gas 12 within the first section 143 of the first chamber 120 is maintained at substantially the same temperature as the temperature of the pipeline gas 14 flowing through the pipeline 16.

The second solenoid valve 142 is closed when sample gas 12 is filling the first section 143 of the hollow coil 120' to pipeline pressure $P_L$. When the sample gas 12 pressure in the first section 143 reaches $P_L$, the first solenoid valve 122 closes and the second solenoid valve 142 opens. The sample gas 12 pressure in the first section 143 drops abruptly because the sample gas 12 pressure in the second volume 144 is less than the sample gas 12 pressure in the first section 143 at that instant. The volume of the second section 144 is such that the pressure in both chambers will stabilize at a pressure slightly higher than the starting pressure $P_1$. The pressure in both sections 143 and 144 combined then decays to $P_1$ at which time the timer 134 begins and measures the time interval $t_m$ for the pressure in both sections 143 and 144 to decay from the starting pressure $P_1$ to the stopping pressures $P_2$.

In this embodiment where the first chamber has a first 143 and a second 144 section, it is necessary for the sample gas pressure in the first section 143 to reach $P_L$ while being maintained at substantially the same temperature as the pipeline gas 14, but it is not necessary for the sample gas pressure in the second section 144 to reach $P_L$.

This configuration allows rapid containment of the sample gas 12 within the fixed volume of the first section 143 of the hollow coil 120' at pipeline pressure $P_L$ and alleviates the need to wait for the sample gas 12 pressure to slowly decay to the starting pressure $P_1$. Moreover, the second section 144 of the hollow coil 120' has a much larger volume than the first section 143 (i.e., about 12 fold) and thus the sample gas 12 pressure within the second section 144 does not fluctuate substantially. The flowrate through the flow controller 126 is thus easier to maintain at the selected rate.

Still referring to FIG. 7, an arching sample gas feed 146 along with a valve 148 and a valve 150 are used to remove debris from the sample gas 12 before the sample gas 12 flows to the hollow coil 120'. The low velocity in the rising section containing the valve 148 precludes particles from reaching the arch in the arching sample gas feed 146. Instead, the particles fall into a lower section of the pipe containing the valve 150. Periodically, the valve 150 can be opened to blow the collected debris from the lower section of the pipe through a blow hole 152. A filter 154 is also installed on the arching sample gas feed 146 to remove debris from the sample gas 12.

The following analysis is recited to emphasize the significance that $$P_m = \frac{P_L}{2}$$

and to also explain additional features of this embodiment of the invention that further improve the accuracy of the invention.

The total derivative of pressure with respect to time must account for density changes as well as molar flow and is given by:

$$\left(\frac{dP}{dt}\right)_T = \frac{RT\left(Z + \left(\frac{\delta Z}{\delta \rho}\right)_T\right)}{M_w V} \omega_m \quad (23)$$

where $$\left(\frac{dP}{dt}\right)_T$$

is the total derivative of pressure with respect to time at constant temperature T, R is the real gas constant, V is the volume of the first fixed-volume chamber 120 (or the volume of the first section 143 of the hollow coil 120' if the embodiment in FIG. 7 is used), $M_w$ is the molecular weight of the sample gas 12, $\omega_m$ is the mass flowrate of the sample gas 12, Z is the supercompressibility constant for the gas, and $$\left(\frac{\delta Z}{\delta \rho}\right)_T$$

is the partial derivative of Z at constant temperature T with respect to the molar density of the gas $\rho$.

The supercompressibility constant Z, which describes the dynamics of compressible gas, can be closely approximated by expanding the virial equation of state through the first three terms:

$$Z = 1 + bP + cP^2 = 1 + B\rho + C\rho^2 \quad (24)$$

where $\rho$ is gas density, P is the absolute gas pressure, B and C are the second and third density virial coefficients of the gas, and b and c are the second and third pressure virial coefficients of the gas. The virial coefficients depend on gas temperature and composition. The density virial coefficients are related to the pressure virial coefficients according to thermodynamic relations:

$$b = \frac{B}{RT} \quad (25)$$

$$c = \frac{(C - B^2)}{R^2 T^2} \quad (26)$$

where R is the real gas constant and T is the absolute temperature of the gas.

It follows from Eqs. (23), (24), (25) and (26) that the total derivative $$\left(\frac{dP}{dt}\right)_T$$

for the sample gas 12 is:

$$\left(\frac{dP}{dt}\right)_T = \frac{RT(1 + 2bP_m + (3c + b^2)P_m)}{M_w V} \omega_m \quad (27)$$

In the present invention, the derivative $$\left(\frac{dP}{dt}\right)_T$$

is represented by:

$$\left(\frac{dP}{dt}\right)_T = \frac{P_1 - P_2}{t_m} \quad (28)$$

where $t_m$ is the time interval for the sample gas pressure in the first chamber 120 to drop from $P_1$ to $P_2$. Substituting Eq. (28) into Eq. (27) and solving for the mass flowrate of the sample gas 12, $\omega_m$, results in:

$$\omega_m = \frac{M_w V(P_1 - P_2)}{RT(1 + 2bP_m + (3c + b^2)P_m^2 t_m)} \quad (29)$$

Now, the mass flowrate of the pipeline gas 14 is given by:

$$\omega_t = \frac{\rho f_t}{K_t} \quad (30)$$

where $f_t$ is the frequency signal that the turbine meter 110 communicates to control system 20, and $K_t$ is the turbine meter calibration constant relating turbine frequency $f_t$ to volumetric flowrate (i.e., cycles/unit volume).

Using the real gas law and the virial equations of state, Eq. (30) becomes:

$$\omega_t = \frac{f_t}{K_t} \frac{P_L M_w}{RT(1 + bP_L + cP_L^2)} \quad (31)$$

where $P_L$ is the absolute pressure of pipeline gas 14. Dividing Eq. (31) by Eq. (29) results in:

$$\frac{\omega_t}{\omega_m} = \frac{P_L f_t t_m (1 + 2bP_m + (3c + b^2)P_m^2)}{K_t V(P_1 - P_2)(1 + bP_L + cP_L^2)} \quad (32)$$

From Eq. (32), it is apparent that the effects of supercompressibility, first represented by the second pressure virial coefficient b, are minimized if $P_m$ is approximately equal to $$\frac{P_L}{2}.$$

The accuracy of the invention is not compromised significantly provided that the measuring pressure $P_m$ is within a few percent of half the pipeline pressure $P_L$ because the second virial coefficient b is of the order $10^{-3}$ atm$^{-1}$.

Figure 8:
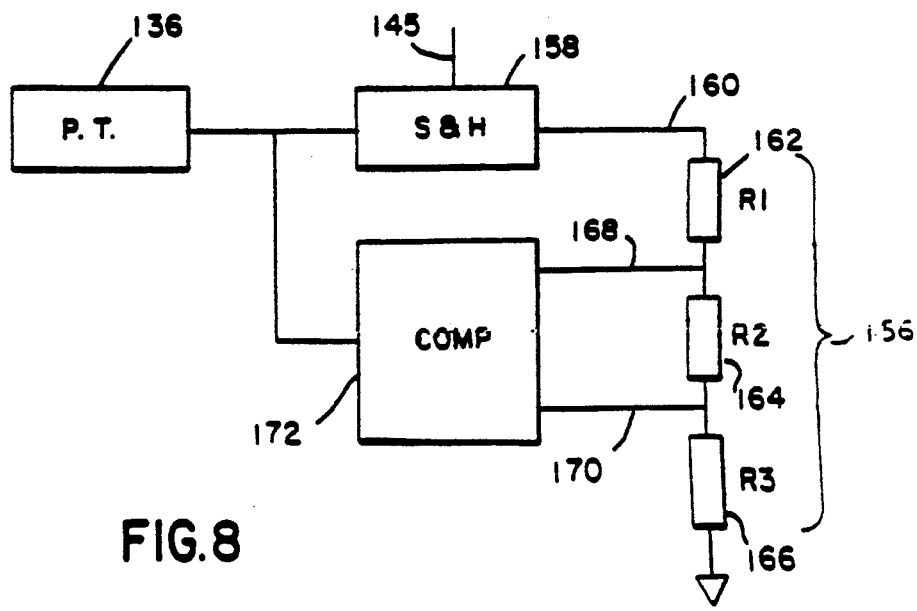
FIG. 8 is a schematic drawing showing a circuit used in the embodiment shown in FIG. 5.

Referring to FIG. 8, the starting $P_1$ and the stopping $P_2$ pressures are determined by a resistor string 156. The pressure sensor 136 senses the pressure in the first chamber 120 (or in the first section 143 of the hollow coil 120' if the embodiment shown in FIG. 7 is used) and communicates the data to an associated sample and hold circuit 158 and to the control system 20. The control system 20 determines when the sample gas 12 pressure in the first chamber 120 stabilizes at a maximum pressure, i.e., at the pipeline gas 14 pressure $P_L$, and sends a signal 145 indicating that maximum pressure to the sample and hold circuit 158. The sample and hold circuit 158 memorizes the value of the maximum pressure in the first chamber 120' for each sampling cycle 124. The circuit 158 is cleared at the end of each sampling cycle 124 after it receives a signal that the first solenoid valve 122 has opened.

An output voltage 160 from the sample and hold circuit 158 represents the maximum chamber pressure (i.e., $P_L$) and leads to the grounded resistor string 156. The output voltage 160 is split by the resistors 162, 164, and 166. The output voltage 160 drops across resistor 162 to the $P_1$ reference voltage 168 and further drops across resistor 164 to the $P_2$ reference voltage 170. The resistance of the resistor 162, R1, is equivalent to the resistance of the resistor 166, R3, so that the measurement pressure $P_m$ is $$\frac{P_L}{2}.$$

Further, the resistance of resistor 162 and 166, R1 and R3, should be much greater than the resistance of resistor 164 so that the value of $(P_1 - P_2)$ is small compared to $P_L$. A ratio $$K_P = \frac{P_L}{(P_1 - P_2)}$$

is then represented by $$\frac{R1 + R2 + R3}{R2}$$

The $P_1$ and $P_2$ reference voltages (168 and 170) are stored in a comparator 172 which compares these values to a signal from the pressure sensor 136. When the pressure sensor 136 signals that the pressure in the first chamber 120 has dropped to $P_1$, the comparator 172 activates the timer 134. When the pressure drops to $P_2$, the comparator 172 signals the timer 134 to stop.

Equation (32) can then be rewritten as:

$$\frac{\omega_t}{\omega_m} = \frac{K_P f_t t_m \left(1 + bP_L + \frac{(3c + b^2)}{4} P_L^2\right)}{K_t V(1 + bP_L + cP_L^2)} \quad (33)$$

and since higher order terms are very small, Eq. (28) can be reduced to:

$$S = \frac{\omega_t}{\omega_m} = \frac{K_P f_t t_m}{K_t V} \left(1 + \frac{(b^2 - c)}{4} P_L^2\right) \quad (34)$$

where S is a splitting ratio. Since the sample gas 12 flowrate $\omega_m$ is measured while the sample gas 12 is at pipeline conditions, the splitting ratio $$S = \frac{\omega_t}{\omega_m}$$

is also equal to $$\frac{Q_f}{Q_{f'}}$$

because the density of the sample gas 12 is the same as the pipeline gas 14 in the pipeline 16. The sample gas 12 volumetric flowrate $Q_{f'}$ can then be determined by multiplying $Q_f$ as measured by the turbine meter 110 by $$\frac{Q_f}{Q_{f'}} \text{ (i.e., } S^{-1}\text{)}.$$

The second term $$\frac{(b^2 - c)}{4} P_L^2$$

in Eq. (34) is an error correction term and is significant at high pressures. For methane gas, b is about 0.0024 and c is about $3.1 \times 10^{-6}$ when pressure is measured in bars. If $P_L$ is 30 bar (i.e., 440 psia), the error associated with the second term is about 0.25%. The error associated by the second term $$\frac{(b^2 - c)}{4} P_L^2$$

in Eq. (34) can be reduced by determining values for b and c. It is convenient to rewrite the second term $$\frac{(b^2 - c)}{4} P_L^2$$

in terms of the third density virial coefficient C:

$$\frac{(b^2 - c)}{4} P_L^2 = \left(2b^2 - \frac{C}{(RT)^2}\right)\frac{P_L^2}{4} \quad (35)$$

The value of b can be determined by a second measurement at low absolute pressure. For low absolute pressure, the total derivative of pressure with respect to time $$\left(\frac{dP}{dt}\right)_T$$

can be written in the form of Eq. (27) but neglecting the third virial coefficient c:

$$\left(\frac{dP}{dt}\right)_T = \frac{RT(1 + 2bP_Y)}{M_w V}\omega_m \quad (36)$$

where $P_Y$ is a low pressure. The sample gas 12 mass flowrates $\omega_m$ in Eqs. (27) and (36) are the same as selected by the flow controller 126. The second virial coefficient b can be estimated by combining and simplifying Eqs. (27) and (36):

$$b = \frac{\dot{P}_m - \dot{P}_Y}{2(P_m \dot{P}_Y - P_Y \dot{P}_m)} \quad (37)$$

where $\dot{P}_m$ is the total pressure derivative at $P_m$ and $\dot{P}_Y$ is the total pressure derivative at low pressure. Equation (37) can be expressed in terms of pressures and time interval measurements:

$$b = \frac{\frac{P_1 - P_2}{t} - \frac{P_{Y1} - P_{Y2}}{t_Y}}{2\left(P_m \frac{P_{Y1} - P_{Y2}}{t_Y} - P_Y \frac{P_1 - P_2}{t_m}\right)} \quad (38)$$

where $t_Y$ is the time interval for a pressure decay at low pressure (i.e., $P_{Y1} - P_{Y2}$) and is determined in a manner similar to the interval $t_m$.

Equations (37) and (38) assume that the volume in which the pressure drops $P_1 - P_2$ and $P_{Y1} - P_{Y2}$ occur is constant. This assumption is true if the pressure drops are both measured in the first chamber 120 (or in the first section 143 of the hollow coil 120' if the embodiment shown in FIG. 7 is used), but at different times.

Figure 9:
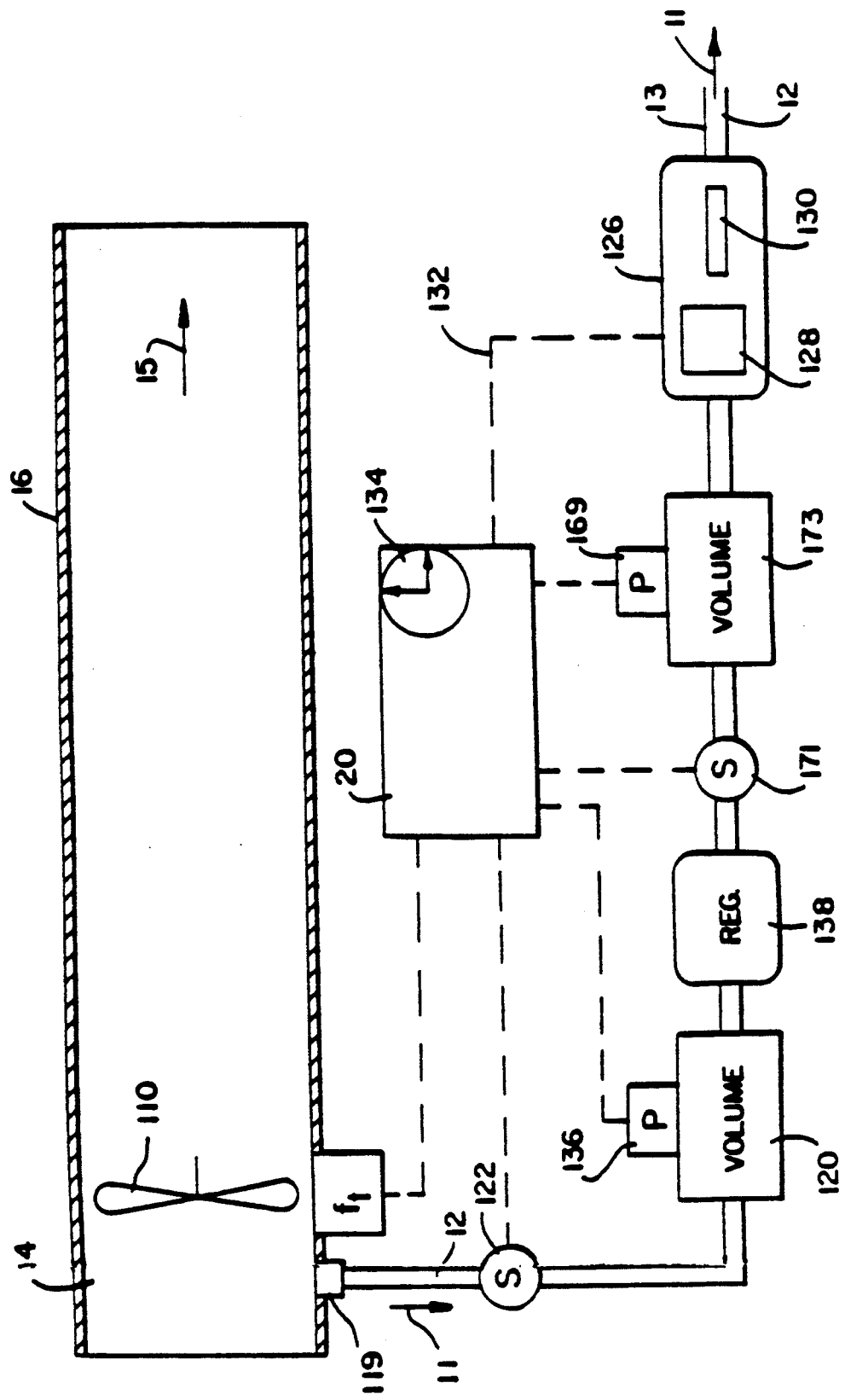
FIG. 9 is a schematic drawing showing the embodiment shown in FIG. 5 with a second chamber.

Referring to FIG. 9, it may be preferable in some circumstances to use a second fixed-volume chamber 173 downstream of the first chamber 120 and measure the low pressure drop $(P_{Y1} - P_{Y2})$ in the second chamber 173. In FIG. 9, the sample gas 12 pressure is reduced significantly as the sample gas 12 flows from the first chamber 120 to the second chamber 173 by an in-line pressure regulator 138. A third solenoid valve 171 is located in line between the pressure regulator 138 and the second chamber 173. A pressure sensor 169 measures the sample gas pressure in the second chamber 173. The timer 134 measures the time interval $t_Y$ for the pressure to decay from $P_{Y1}$ to $P_{Y2}$ in the second chamber 173. An advantage of the configuration shown in FIG. 9 is a reduction in waiting time for the sample gas pressure to decay to the low pressure $P_{Y1}$. If the configuration shown in FIG. 9 is used and the volume of the second chamber 173 is different than the volume of the first chamber 120 (or the volume of the first section 143 of the hollow coil 120' if the embodiment shown in FIG. 7 is used), Eqs. (37) and (38) should be replaced with:

$$b = \frac{V\dot{P}_m - V_Y \dot{P}_Y}{2(P_1 V_Y \dot{P}_Y - P_{Y1} V \dot{P}_m)} \quad (39)$$

and:

$$b = \frac{V\frac{P_1 - P_2}{t_m} - V_Y \frac{P_{Y1} - P_{Y2}}{t_Y}}{2\left(P_m V_Y \frac{P_{Y1} - P_{Y2}}{t_Y} - P_Y V \frac{P_1 P_2}{t_m}\right)} \quad (40)$$

where V is the volume of the first chamber 120 (or the volume of the first section 143 of the hollow coil 120' if the embodiment shown in FIG. 7 is used) and $V_Y$ is the volume of the second chamber 173.

For natural gas, which usually consists of 80% or more natural gas, the value of $$\frac{C}{4(RT)^2}$$

in Eq. (35) can be approximated by a relationship in the form of $KP^2$ where K is a constant and P is pressure. In Table 1 are listed values of c and of $$\frac{c}{4(RT)^2}$$

for pure methane and also for mixtures containing 80% methane each at 45° F. and 81° F. The values in Table 1 were obtained from published data, such as the Brugge Data from Texas A&M, and from interpolating the published data using thermodynamic mixing rules for virial coefficients.

TABLE 1

| Mixture | c @280° K. cm$^6$/mol$^2$ | c @300° K. cm$^6$/mol$^2$ | C/4(RT)$^2$ @280° K. 10$^6$ atm$^{-2}$ | C/4(RT)$^2$ @300° K. 10$^6$ atm$^{-2}$ |
|---|---|---|---|---|
| Methane (CH$_4$) | 2649 | 2438 | 1.256 | 1.007 |
| Ethane (C$_2$H$_6$) | 10774 | 10392 | | |
| 80% CH$_4$; 20% C$_2$H$_6$ | 3714 | 3463 | 1.761 | 1.431 |
| Carbon Dioxide (CO$_2$) | 5636 | 4927 | | |
| 80% CH$_4$; 20% (CO$_2$) | 3130 | 2844 | 1.484 | 1.175 |
| Nitrogen (N$_2$) | 1451 | 1443 | | |
| 80% CH$_4$; 20% N$_2$ | 2371 | 2211 | 1.124 | 0.913 |

The splitting ratio $$S = \frac{\omega_t}{\omega_m}$$

is computed in real time by the control system 20 in accordance with Eq. (34). In the calculation, $K_P$, $K_t$, and V are constants stored within the control system 20 and the turbine frequency $f_t$, and the time interval $t_m$ are communicated to the control system 20 for each sampling cycle 124. The second virial coefficient b is estimated by measuring the time interval $t_T$ for a pressure decay at low pressure and using Eq. (38) or (39), whichever is appropriate. The third virial coefficient c is estimated using data from Table 1. Finally, $P_L$ is measured by the pressure sensor 136 and relayed to the control system 20.

Method and Apparatus for Measuring $Q_f$ With a Capillary Tube

This way for measuring the sample gas 12 flowrate $Q_f$ would typically be used with a pipeline gas volumetric flowmeter 22 of the type considered to be a differential pressure meter. The apparatus and method of this way of measuring $Q_f$ are depicted in FIGS. 10–17.

Figure 10:
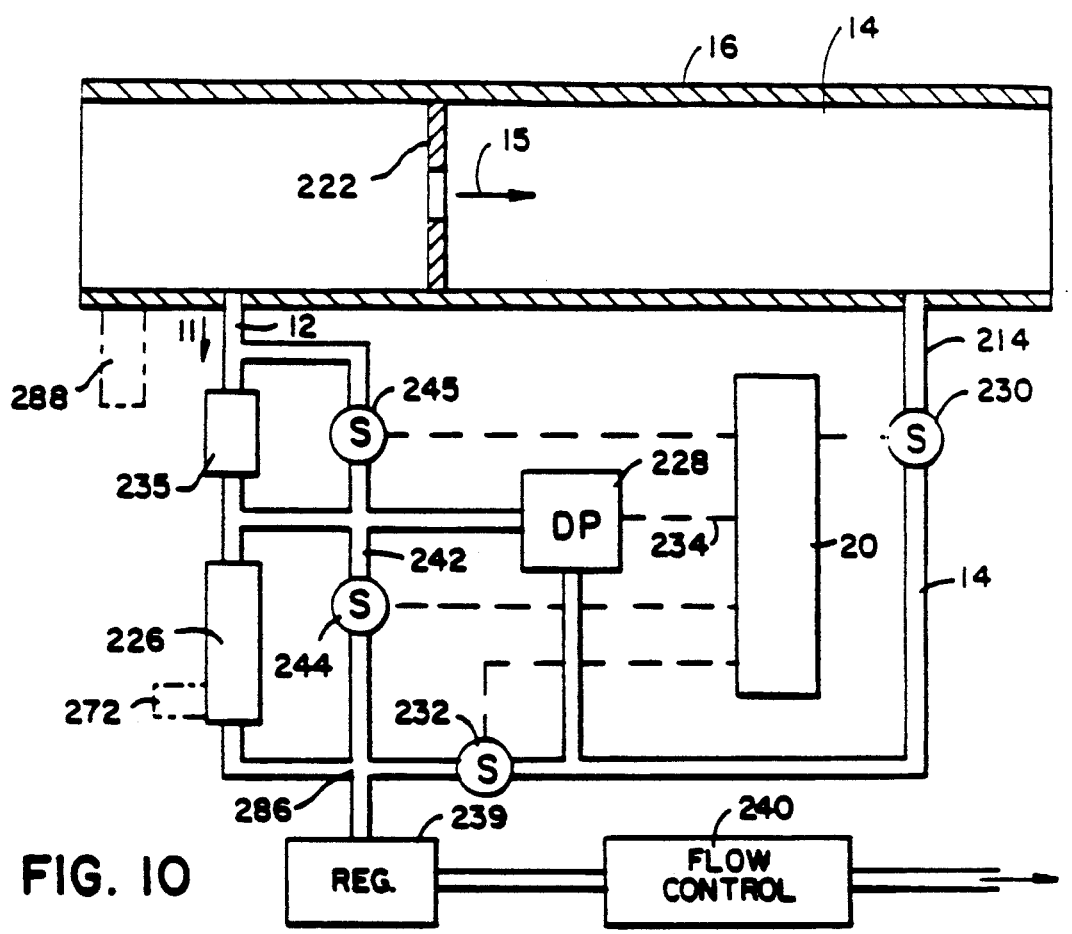
FIG. 10 is another preferred embodiment of the present invention which uses a capillary tube.

Referring to FIG. 10, the present invention has a first 212 and a second port 214 for tapping pipeline gas 14 flowing through a pipeline 16 in the direction shown by arrow 15. The pipeline 16 typically has an internal orifice 222 and the pressure of the pipeline gas 14 changes as it flows across the orifice 222. Other differential pressure volumetric flow monitoring devices that produce a pressure differential and can be calibrated, including but not limited to venturi devices or nozzles, can be used in place of an internal orifice 222, but an internal orifice is preferred.

Figure 11:
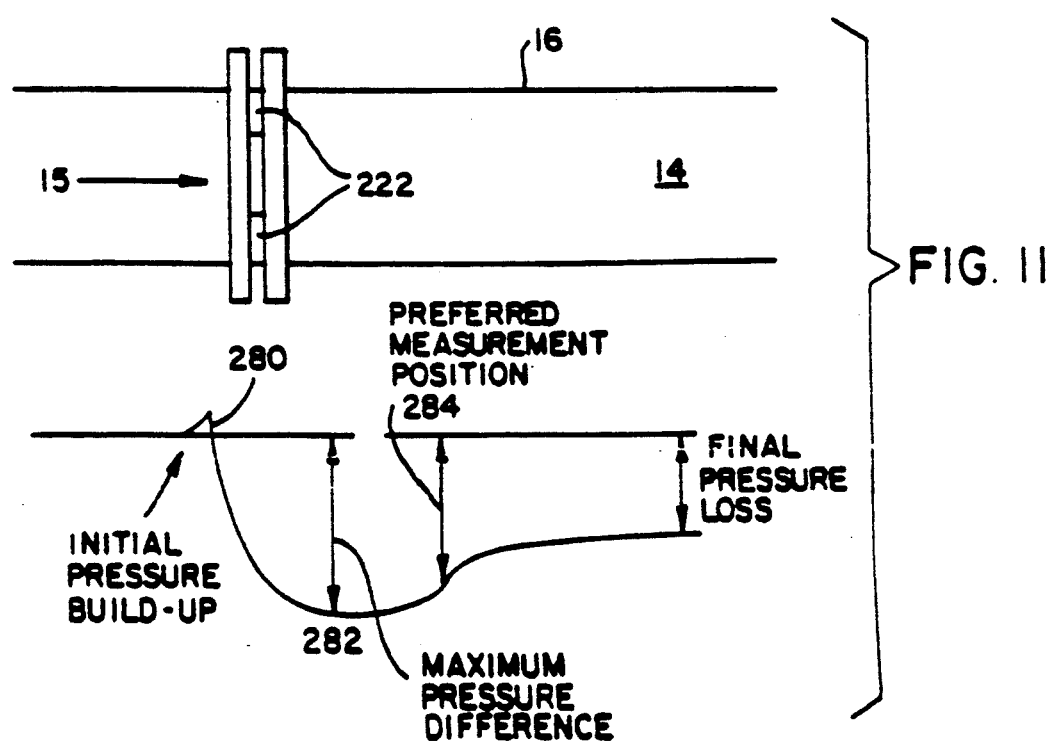
FIG. 11 is a schematic drawing showing pipeline gas pressure as a pipeline gas flows through a differential pressure orifice.

It should also be noted that, as depicted in FIG. 11, pressure differentials of pipeline gas 14 across an orifice 222 or other such device is dynamic in nature, and not necessarily constant. In FIG. 11, as the flow 15 of the pipeline gas 14 approaches the orifice 222, the gas pressure rises 280 slightly. The flow 15 is constricted to flow through the orifice 222 and continues to constrict after it passes through the orifice until it reaches a low pressure point 282. As the flow 15 constricts, flow speed increases and consequently the flow pressure drops. Flow pressure also drops due to frictional losses. As the flow 15 widens to fill the pipeline 16 downstream of the low pressure point 282, flow speed reduces and gas pressure recovers to a value equal to the initial flow pressure, $P_o$, less frictional losses. Differential pressure flow meters are most sensitive if the pressure differential measured is the initial pipeline pressure at the low pressure point 282. The physical location of the low pressure point 282, however, varies significantly with flow velocity and it is therefore preferred to monitor the flow pressure at an intermediate flow recovery point 284, because such a measurement is less likely to be inaccurate due to fluctuations in flow velocity. In the art, there are three kinds of taps for measuring pressure differentials, each for measuring the pressure at various stages after an orifice; flange taps, vena contracta taps, and pipe taps. It should be emphasized, however, that the present invention can be used with any type of differential pressure flowmeter, including but not limited to an orifice plate 222, venturi, or nozzle, and without regard to the specific pressure difference which is monitored by the meter.

Referring to FIG. 10, the first port 212 taps sample gas 12 from the pipeline before it flows through the orifice 222. The flow of sample gas 12 is shown through the apparatus as flowing in the direction of arrows 11. The sample gas 12 is routed to a capillary tube 226. Capillary tubes are made in many forms and the term capillary tube as used herein means a device for obtaining a very small controlled flowrate. As will be apparent to one skilled in the art, the present invention does not require that the capillary tube 226 be a conventional capillary tube, or a tortuous path capillary tube 226' as described below. Rather, any apparatus that allows the flow of sample gas 12 and produces a pressure differential is sufficient.

It is preferred, however, that the capillary tube 226 be a tortuous path capillary tube 226' as shown in FIGS. 12 and 13. Referring to FIGS. 12 and 13, the flow of sample gas 12 through the tortuous path capillary tube 226' is in the direction shown by arrows 261. The sample gas 12 is not able to flow through the tortuous path capillary tube 226' as straight-line, laminar flow because flow obstruction discs 258 obstruct the flow 261. Sample gas 12 can flow through the tortuous path capillary tube 226' only by flowing through flow holes 259 which extend through each obstruction disc 258. Each flow hole 259 is eccentrically located on a disc 258 and misaligned with adjacent flow holes 259 to create a tortuous flow path through the capillary tube 226'. A tortuous path capillary tube 226' with this sort of configuration has a more stable discharge coefficient, $C_c$, in the flow regime of interest as shown in FIG. 14. Testing has shown that it is preferred that the obstruction discs 258 be 0.060″ thick and that the flow holes 259 have a 0.010″ diameter. The obstruction discs 258 should be spaced apart a distance at least 5 to 6 times the thickness of the discs 258.

Referring again to FIG. 10, the second port 214 taps gas from the pipeline 16 after it flows through the orifice 222.

A differential pressure cell (DP cell) 228 measures a pipeline gas 14 pressure differential across the orifice 222, $\Delta P_o$, and a sample gas 12 pressure differential across the capillary tube 226, $\Delta P_c$. The DP cell accomplishes this by measuring the pressure difference between the sample gas 12 before it flows through the capillary tube 226 and (i) the pipeline gas 14 after it flows through the orifice 222 or (ii) the sample gas 12 after it flows through capillary tube 226.

A first solenoid valve 230 is located between the DP cell 228 and the second port 214. A second solenoid valve 232 is located between the DP cell 228 and the capillary tube outlet 238. A control system 20 communicates to the first 230 and second 232 solenoid valves to coordinate them so that the second 232 valve is closed when the first valve 230 is open and the first valve 230 is closed when the second valve 232 is open.

The DP cell 228 detects the pressure differential across the orifice 222 when the first solenoid valve 230 is open and the second solenoid valve 232 is closed. The DP cell 228 detects the pressure differential across the capillary tube 226 when the second solenoid valve 232 is open and the first solenoid valve 230 is closed. The DP cell 228 provides an electrical signal 234 in direct proportion to the measured pressure differential to the control system 20.

The present invention preferably employs a single DP cell 228, but using more than one DP cell 228 is possible. By using two DP cells 228, each DP cell 228 can individually monitor a separate pressure drop: one to continuously monitor the pressure drop across the orifice 222 and one to continuously monitor the pressure drop across the capillary tube 226. A single DP cell 228 is preferred, however, because it provides common mode rejection.

Referring to FIG. 10, zero offset error in the DP cell 228 can be completely eliminated by adding a line 242 with a third solenoid valve 244 for flowing sample gas 12 around the capillary tube 226. When the third 244 solenoid valve is opened, the pressure across the DP cell 228 is zero and the zero offset is the residual DP cell signal 234. The zero offset is communicated to the control system 20 where it is stored and subtracted from subsequent DP cell signals 234 taken when the third solenoid valve 244 is closed. In this manner, offset error is totally eliminated. The third solenoid valve 244 can be opened periodically for calibration.

A flow controller 240 for maintaining a substantially constant flow of sample gas 12 from the capillary tube 226 is located downstream of the capillary tube 226 and downstream from the branch 286 of the sample line where the second solenoid valve 232 is attached. Flow controllers are known in the art and an electronically adjustable pressure regulator followed by a capillary tube is suitable for this application. A pressure regulator 239 can be installed in the sample gas 12 line after the point 286 and before the flow controller 240 to reduce the pressure of the sample gas 12 at the flow controller 240.

The sample gas 12 must be maintained at a temperature substantially equal to the temperature of the pipeline gas 14 when it is in the capillary tube 226. If the temperature of the sample gas 12 is maintained at substantially the same temperature as the pipeline gas 14, the need to compensate the effects of supercompressibility can be avoided since gas density is maintained in the sample gas 12.

Figure 15:
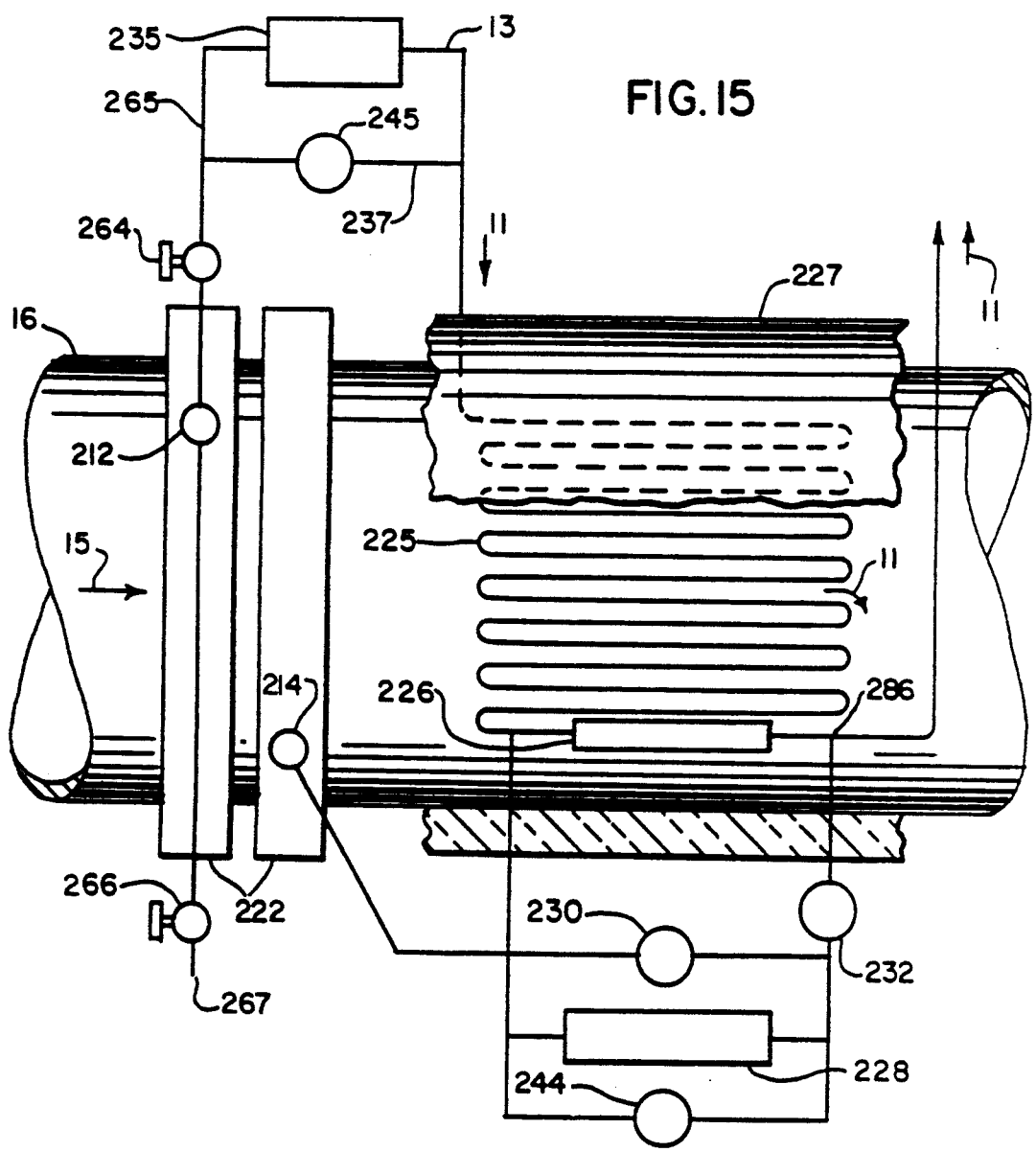
FIG. 15 is a schematic view showing the embodiment of FIG. 10 mounted to a pipeline.

Referring to FIG. 15, the preferred method of maintaining the proper sample gas 12 temperature within the capillary tube 226 involves routing the sample gas 12 to the capillary tube 226 through a serpentined line 225. Both the serpentined line 225 and the capillary tube 226 are mounted in intimate contact with the outside surface of the pipeline 16. Insulation 227 should be placed around the serpentined line 225, the capillary tube 226 and the pipeline 16 to facilitate temperature equalization. With this configuration, the temperature of the sample gas 12 within the capillary tube is maintained at substantially the same temperature as the temperature of the gas 14 flowing through the pipeline 16.

There are other, less preferred, methods for maintaining the proper sample gas 12 temperature within the capillary tube 226. One such method is to insert the capillary tube 226 inside of the pipeline 16.

It is not necessary to maintain the sample gas 12 temperature as substantially equal to the temperature of the gas 14 flowing through the pipeline 16 after the sample gas 12 exits the capillary tube 226. For that reason, the components of the invention which are not shown to be mounted on or at the pipeline 16 in FIG. 15 are not pipeline mounted, but rather wall mounted.

An arching sample gas feed 265 along with a valve 264 and a valve 266 are used to remove debris entering the sample line at port 212. The low velocity in the rising section containing the valve 264 precludes particles from reaching the arch in the arching sample gas feed 265. Instead, the particles fall into a lower section of the pipe containing the valve 266. Periodically, the valve 266 can be opened to blow the collected debris from the lower section of the pipe through a blow hole 267.

A filter 235 is also installed in the arching sample gas feed 265 to remove debris from the sample gas 13 line. If the filter 235 becomes clogged, the invention may become ineffective so line 237 is installed around the filter 235 with an in-line solenoid valve 245. Periodically, valve 245 is opened, and the DP cell 228 in effect measures the additional pressure drop across the filter 235. The pressure drop across the filter 235 as measured can be used to correct the differential pressure valves across the capillary tube 226 that are measured by the DP cell 228 during operation. If the pressure drop across the filter 235 is too large, the filter should be replaced.

The mass flowrate of pipeline gas 14 through the orifice 222 in the pipeline 16 can be represented by:

$$\omega_o = F_o E_v Y_o C_o \sqrt{\rho_o \Delta P_o} \tag{41}$$

where $F_o$ is the orifice 222 scaling constant, $E_v$ is the velocity approach factor, $Y_o$ is the expansion factor for the pipeline gas 14, $C_o$ is the orifice 222 discharge coefficient, $\rho_o$ is the density of the pipeline gas 14 and $\Delta P_o$ is the pipeline gas 14 pressure differential.

The orifice scaling constant, $F_o$, and the velocity approach factor, $E_v =$ $$\left( \frac{1}{\sqrt{1 - \beta^4}} \right),$$

are constants that depend on orifice geometry. For example, $\beta$, for a circular orifice in a circular pipe, is defined as $$\frac{d}{D}$$

where d is the diameter across the orifice and D is the diameter of the pipe.

The gas expansion coefficient, $Y_o$, and the orifice discharge coefficient, $C_o$ in Eq. (41) can, however, vary with the pipeline gas 14 pressure or flowrate. The expansion coefficient, $Y_o$, for orifice 222 plates can be represented as:

$$Y_o = 1 - (0.41 + 0.35\beta^4)\frac{\Delta P_o}{kP_o} \qquad (42)$$

where $P_o$ is the absolute pressure of the pipeline gas 14, and k is the isentropic exponent of the gas 14.

The orifice discharge coefficient, $C_o$, is usually, and properly defined as a function of Reynold's Number, $$\left(R_e = \frac{\rho V D}{\mu}\right);$$

where $\rho$ is gas density, V is flow velocity, D is the pipe diameter or other characteristic length of the flow field, and $\mu$ is the dynamic viscosity of the gas 14). The standard AGA-3 form for representing the discharge coefficient, $C_o$, is:

$$C_o = C_{io} + K_o\left[\frac{1}{R_{eD}}\right]^{0.7} \qquad (43)$$

where $R_{eD}$ is the Reynold's Number of the pipeline gas 14 flow, $C_{io}$ represents the discharge coefficient at infinite $R_{eD}$ and $K_o$ is a coefficient for correction at finite $R_{eD}$.

In both Eqs. (42) and (43), the second terms are small compared to the first terms. In Eq. (42), the second term $$(0.41 + 0.35\,\beta^4)\frac{\Delta P_o}{kP_o}$$

is normally about 0.02 as compared to unity. In Eq. (43), the second term $$K_o\left(\frac{1}{R_{eD}}\right)$$

for most orifice installations is about 0.5% of $C_{io}$ or less.

The mass flowrate of the sample gas 12 through the capillary tube 226 is represented by:

$$\bar{\omega}_c = F_c Y_c C_c \sqrt{\rho_c \Delta P_o} \qquad (44)$$

where $F_c$ is the capillary tube scaling constant, $Y_c$ is the sample gas 12 expansion factor, $C_c$ is the capillary tube discharge coefficient, $\rho_c$ is the density of the sample gas 12 in the capillary tube and $\Delta P_c$ is the sample gas 12 pressure differential as it flows through the capillary tube 226.

The form of Eq. (44) is similar to the form of Eq. (41), except that the approach velocity factor, $E_v$, which appears in Eq. (41) is taken to be unity in Eq. (44) because $\beta$ is very small for the capillary tube 226. The value of the capillary tube scaling constant, $F_c$, does not depend on the flowrate or pressure of the sample gas 12, but rather is a constant that depends on capillary tube 226 geometry.

The sample gas 12 expansion factor, $Y_c$, is represented by:

$$Y_c = 1 - 0.41\frac{\Delta P_c}{kP_c} \qquad (45)$$

where $P_c$ is the absolute pressure of the sample gas 12, and k is the isentropic exponent of the sample gas 12. The form of Eq. (45) is similar to the form of Eq. (42), except that the $0.35\beta^4$ term in Eq. (42) is taken to be zero in Eq. (45) because $\beta$ is very small for the capillary tube 226.

It is preferred that the capillary tube 226 be a tortuous path capillary tube 226' as discussed above. The capillary tube discharge coefficient, $C_c$, for a tortuous path capillary tube 226' is represented by:

$$C_c = \frac{C_{ic}}{\sqrt{n}} + \frac{K_c}{\sqrt{n}}\left[\frac{1}{R_{eC}}\right]^{0.7} \qquad (46)$$

where $R_{eC}$ is the Reynold's Number of the sample gas 12 flow, n is the number of obstruction discs 258 within the tortuous path capillary tube 226', $C_{ic}$ represents a universal tortuous path capillary tube 226' discharge coefficient at infinite $R_{eC}$, and $K_c$ is a number for correction at finite $R_{eC}$.

As with Eqs. (42) and (43), the second term in Eqs. (45) and (46) are small compared to the first terms. The second term in Eq. (45), $$0.41\frac{\Delta P_c}{kP_c},$$

is about 0.02 as compared to unity and the second term in Eq. (46), $$\frac{K_c}{\sqrt{n}}\left[\frac{1}{R_{eD}}\right]^{0.7},$$

is about 5% of $$\frac{C_{ic}}{\sqrt{n}}.$$

The fact that the second terms in Eqs. (42), (43), (45) and (46) are much smaller than the first terms in these equations relaxes the necessary accuracy in determining the value of the second terms. For instance, a 10% error in determining a second term that has a value of only 2% of the first term results in an overall error of 0.2%. Testing has shown that Eq. (46) is very accurate for tortuous path capillary tubes 226'. Testing of tortuous path capillary tubes 226' also shows that the coefficients $C_{ic}$ and $K_c$ do not change with the number of obstruction discs 258 within the tortuous path capillary tube 226'.

The ratio of the mass flowrate of the pipeline gas 14, $\bar{\omega}_o$, compared to the mass flowrate of the sample gas 12, $\bar{\omega}_c$, is represented by dividing Eq. (41) by Eq. (44):

$$S = \frac{F_o E_v Y_o C_o \sqrt{\rho_o \Delta P_o}}{F_c Y_c C_c \sqrt{\rho_c \Delta P_c}} \quad (47)$$

where S is splitting variable that is $$\frac{\omega_o}{\omega_c}$$

if computed properly.

Since the pressure conditions across the orifice 222 in the pipeline 16 and across the capillary tube 226 are substantially equivalent and the sample gas 12 flowing through the tube 226 is maintained at substantially the same temperature as the pipeline gas 14, the density of the sample gas 12, $\rho_c$, is equal to the density of the pipeline gas 14, $\rho_o$. The splitting variable S can be represented by:

$$S = \frac{F_o E_v Y_o C_o \sqrt{\Delta P_o}}{F_c Y_c C_c \sqrt{\Delta P_c}} \quad (48)$$

Also, the splitting ratio $$\left(\frac{\omega_O}{\omega_C}\right)$$

is equal to $$\frac{Q_f}{Q_f'}$$

because the density of the sample gas 12 is the same as the pipeline gas 14 in the pipeline 16. The sample gas 12 volumetric flowrate can then be determined by multiplying $Q_f$ as measured by the differential pressure meter (i.e., DP cell 228 across parts 212 and 214) by $$\frac{Q_f'}{Q_f} \text{ (i.e., } S^{-1}).$$

In Eq. (48), $F_o$, $F_c$, and $E_v$ are constants that can be determined from orifice 222 and capillary tube 224 geometry. The ratios $$\left(\frac{Y_o}{Y_c}\right) = Y_r$$

(the gas expansion ratio), $$\left(\frac{C_o}{C_c}\right) = C_r$$

(the discharge coefficient ratio), and $$\sqrt{\frac{\Delta P_o}{\Delta P_c}}$$

(the differential pressure ratio) depend on flow conditions and are measured or calculated to solve Eq. (48) for the mass flow ratio.

In Clingman's U.S. Pat. Nos. 4,125,123; 4,396,299, and 5,016,482, the differential pressure ratio $$\sqrt{\frac{\Delta P_o}{\Delta P_c}}$$

in Eq. (48) is forced to unity by a flow controller. The present invention is different because it seeks to maintain the value of $\Delta P_c$ independent of the pipeline gas 14 pressure differential $\Delta P_o$ and measure the differential pressure ratio $$\sqrt{\frac{\Delta P_o}{\Delta P_c}}.$$

Since $\Delta P_c$ is independent of the pipeline gas 16 pressure differential $\Delta P_o$ in the present invention, difficulties related to fluctuating sample gas 24 flows through the capillary tube 26 are eliminated.

Referring still to Eq. (48), Clingman's U.S. Pat. No. 5,106,482 further employs a capillary tube constructed such that the expansion ratio, $$\left(\frac{Y_o}{Y_c}\right) = Y_r,$$

is always nearly unity. The present invention does not require $Y_r = 1$. Rather, in the preferred embodiment, the present invention computes the ratio $$\left(\frac{Y_o}{Y_c}\right) = Y_r$$

by the following formula:

$$\left(\frac{Y_o}{Y_c}\right) = Y_r = \frac{1 - (0.41 + 0.35\beta^4)\frac{\Delta P_o}{kP_o}}{1 - 0.41\frac{\Delta P_c}{kP_c}} \quad (49)$$

As can be seen in FIG. 10, the absolute pressure of the gas 12 at the capillary tube 226, $P_c$, and the gas 14 at the orifice 222, $P_o$, are identical (i.e., $P_o = P_c$).

When pipeline 16 pressure is high (i.e., 400 to 1000 psia), $Y_r$ is nearly unity because $\Delta P_c$ and $\Delta P_o$ range from 0.3 to 4 or 5 psi. At lower pipeline 16 pressure, however, $Y_r$ might not be close to unity. $Y_r$ is, therefore, computed using Eq. (49). $\Delta P_c$ and $\Delta P_o$ are measured by the DP cell 228 and are needed to solve Eq. (49). The value of the isentropic coefficient, k, ranges from 1.2 to 1.4 for natural gas under the most extreme conditions. A value of 1.3 for k can therefore be used for solving Eq. (49) without causing substantial inaccuracies.

The absolute pipeline pressure $P_o = P_c$ must be determined to solve Eq. (49). Since Eq. (49) is a unity ratio with small correction terms in the numerator and denominator, it is sufficient that the absolute pipeline pressure, $P_o$, be determined to within 5 to 10% accuracy to maintain the accuracy in determining $Y_r$ to within a few percent. There are several methods for measuring the absolute pipeline pressure, $P_o$. One method is to use a pipeline mounted pressure transducer 288 as shown in phantom in FIG. 10. The pressure transducer 288 need not be accurate since the pressure value $P_o$ is used in the correction term in Eq. (49). Pressure transducers 288 suitable for this application are well known in the art and can be purchased from Honeywell, Precision Dynamics or other vendors.

If a tortuous path capillary tube 226' is used, which is preferred, the preferred method for determining the absolute pipeline pressure, $P_o$, and thus $Y_r$ through Eq. (49), requires a second tortuous path capillary tube 290 in connection with the flow controller 240.

Figure 16:
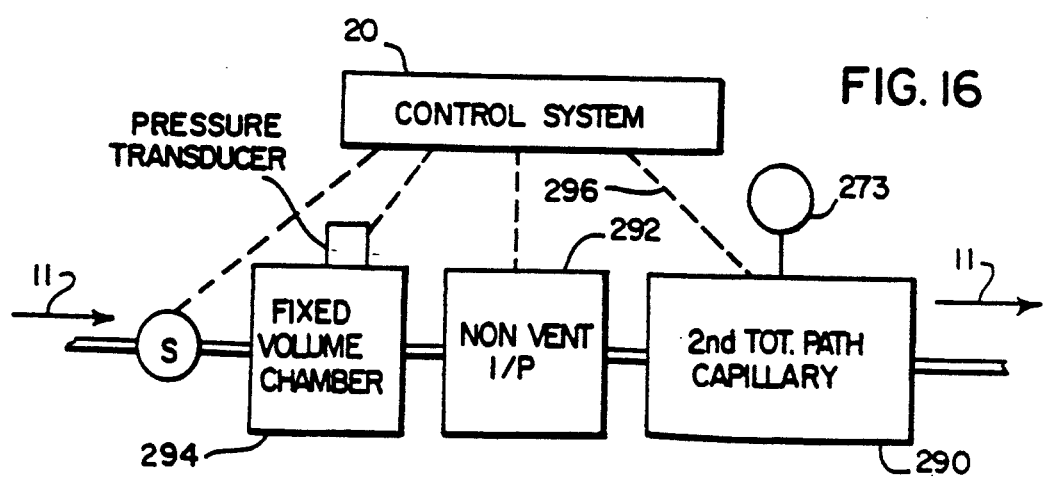
FIG. 16 is a schematic drawing showing additional apparatus that can be used with the embodiment shown in FIG. 10.

Referring to FIG. 16, a flow controller 240 has a second tortuous path capillary tube 290 for determining the absolute pipeline pressure, $P_o$, and an I/P converter 292. The flow controller 240 follows a molar flow meter 294. The molar flow meter 294 of the type described by Kennedy in U.S. Pat. No. 4,285,245 issued on Aug. 25, 1991 is appropriate for use with the flow controller 240. The sample gas 12 flows through the molar flow meter 294, the I/P converter 292 and the second tortuous path capillary tube 290 sequentially. In response to an electrical input signal 296 from the control system 20 (typically ranging from 4 to 20 ma direct current), the I/P converter 292 precisely determines the sample gas 12 pressure causing flow in a second tortuous path capillary tube 290.

Since the sample gas 12 composition is relatively consistent for the period of time it takes the sample gas 12 to flow through the system and the two tortuous path capillary tubes 226' and 290 are in series, the mass flowrate through the tortuous path capillary tube 226' mounted on the pipeline 16, $\bar{\omega}_c$, is substantially equal to the mass flowrate through the second tortuous path capillary tube 290, $\bar{\omega}_s$. Because the tortuous path capillary tube discharge coefficients, $C_c$, are identical for the two tortuous path capillary tubes, except for considerations of the number of obstruction discs 258 in each capillary tube, i.e., $n_c$ and $n_s$, the absolute pipeline pressure, $P_o$, can be represented by:

$$P_o = P_s \left(\frac{Z_c}{Z_s}\right)\left(\frac{n_c}{n_s}\right)\left(\frac{\Delta P_s}{\Delta P_c}\right)\left(\frac{Y_c^2}{Y_s^2}\right)\left(\frac{T_c}{T_s}\right) \quad (50)$$

where $$\left(\frac{Z_c}{Z_s}\right)$$

is the ratio of the compressibility factor of the sample gas 12 in the pipeline mounted tortuous path capillary tube 226' compared to the compressibility factor of the sample gas 12 in the second tortuous path capillary tube 290, $P_s$ is the absolute pressure of the sample gas 12 set by the I/P converter 292, $\Delta P_s$ is the pressure differential across the second tortuous path capillary tube 290 (i.e., $P_s - P_{atm}$). $Y_s$ is the gas expansion coefficient for the second tortuous path capillary tube 290, and $$\left(\frac{T_c}{T_s}\right)$$

is the ratio of the absolute sample gas 12 temperature in the pipeline mounted tortuous path capillary tube 226', $T_c$, compared to the absolute sample gas 12 temperature in the second tortuous path capillary tube 290, $T_s$.

In natural gas applications, the absolute temperature ratio $$\left(\frac{T_c}{T_s}\right)$$

is normally close to unity as determined on the absolute temperature scale. The pressure differential across the pipeline mounted tortuous path capillary tube 226', $\Delta P_c$, is determined by the DP cell 228. The absolute sample gas 12 pressure at the second tortuous path capillary tube 290, $P_s$, and the pressure differential across the second tortuous path capillary tube 290, $\Delta P_s$, are set contemporaneously by the I/P converter 292. The number of obstruction discs 258, $n_c$ and $n_s$, are known constants.

Figure 17:
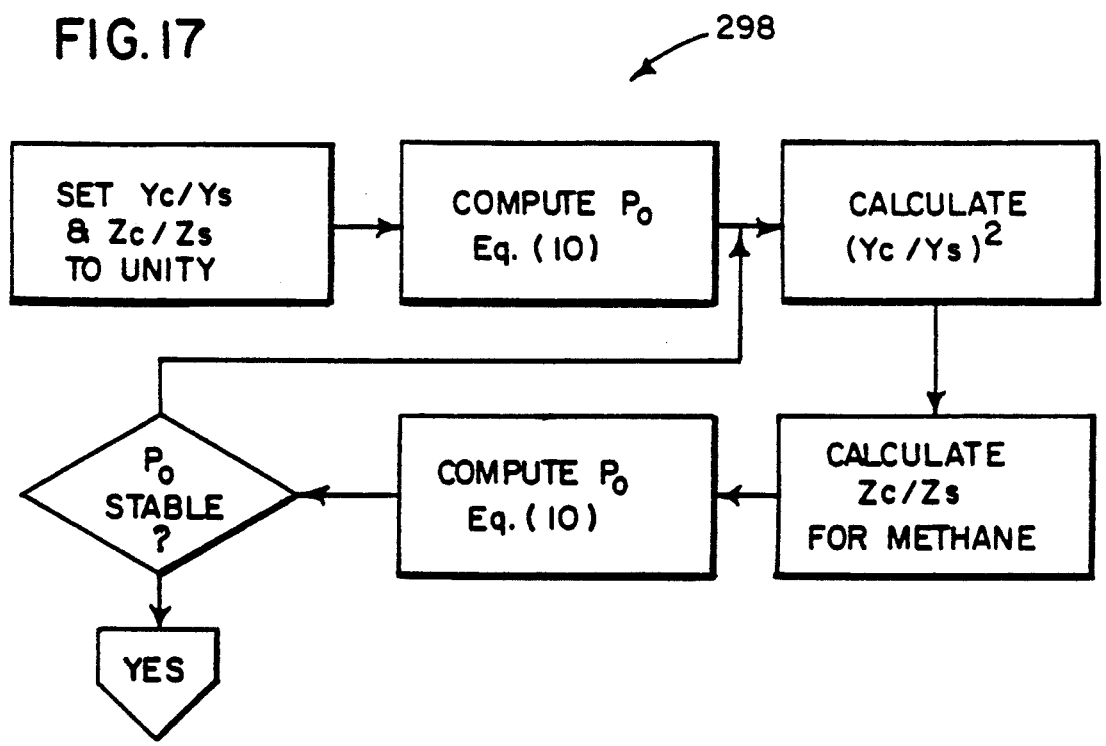
FIG. 17 is a flowchart showing an iterative process used in the embodiment shown in FIG. 10.

Both the ratio of the compressibility factors $$\left(\frac{Z_c}{Z_s}\right)$$

and the ratio of the expansion factors $$\left(\frac{Y_c^2}{Y_s^2}\right)$$

are a function of the absolute pipeline pressure, $P_o$, so an iterative process 298 is used to solve Eq. (50) for $P_o$. The iterative process 298 is shown in FIG. 17. $P_o$ is first approximated by setting the ratios $$\left(\frac{Z_c}{Z_s}\right)$$

and $$\left(\frac{Y_c^2}{Y_s^2}\right)$$

equal to unity and computing Eq. (50). The expansion ratio $$\left(\frac{Y_c^2}{Y_s^2}\right)$$

is then computed using the following equation, which is similar to Eq. (49):

$$\left(\frac{Y_s}{Y_c}\right) = \frac{1 - (0.41)\frac{\Delta P_s}{kP_s}}{1 - 0.41\frac{\Delta P_c}{kP_c}} \quad (51)$$

Note that $\Delta P_c$ is measured by the DP cell 228 and $P_s$ and $\Delta P_s$ are set by the I/P converter 292.

The compressibility ratio $$\left(\frac{Z_c}{Z_s}\right)$$

in Eq. (50) is dependent on gas composition as well as gas pressure and temperature. Since accuracy requirements for Eq. (50) are not stringent and because natural gas normally contains 80% or more methane, the known virial coefficients of methane are used to compute the compressibility ratio $$\left(\frac{Z_c}{Z_s}\right)$$

without a significant loss in accuracy.

The absolute temperature ratio $$\left(\frac{T_c}{T_s}\right)$$

is very close to unity and can be assumed to be unity for the purposes of Eq. (50). Alternatively, the absolute temperatures, $T_c$ and $T_s$, can be measured by temperature detectors 272 and 273 shown in phantom in FIGS. 10 and 16.

After determining the absolute temperature ratio $$\left(\frac{T_c}{T_s}\right)$$

the expansion ratio $$\left(\frac{Y_c^2}{Y_s^2}\right)$$

and the compressibility ratio $$\left(\frac{Z_c}{Z_s}\right)$$

the control system 20 computes Eq. (50) for a new $P_o$ value and compares the new $P_o$ value to the previous $P_o$ value. If the newly computed pipeline pressure, $P_o$, differs from the previous $P_o$ value by more than 2%, the iterative process 298 shown in FIG. 17 is not complete and the process 298 continues by computing a new expansion ratio $$\left(\frac{Y_c^2}{Y_s^2}\right)$$

and compressibility ratio $$\left(\frac{Z_c}{Z_s}\right)$$

using the newly computed $P_o$ value. Iterative $P_o$ values are computed in this manner using the iterative process 298 until the computed $P_o$ value differs from the previously computed $P_o$ value by less than 2%.

Once the pipeline pressure $P_o$ is determined, the expansion factor ratio $$\left(\frac{Y_o}{Y_c}\right) = Y_r$$

needed to solve Eq. (48) is calculated according to Eq. (49).

In order to solve Eq. (47) for the splitting variable S, the discharge coefficient ratio $$\left(\frac{C_o}{C_c}\right) = C_r$$

must also be determined. The orifice discharge coefficient, $C_o$, is defined in Eq. (43) and the capillary tube 226 discharge coefficient, $C_c$, is defined in Eq. (46) The capillary tube 226 discharge coefficient, $C_c$, can be determined by using the control system 20 to periodically vary the flow of the sample gas stream between two preselected flows. The flow controller 240 as shown in FIG. 16, is used to measure the molar flow ratio of the sample gas stream 12. As discussed above, it is appropriate to use the type of molar flow meter 294 described by Kennedy in U.S. Pat. No. 4,285,245.

Pseudo discharge coefficients, based on the molar flows, can be represented for the two preselected flows by:

$$Y_1 C_1^* = \frac{\bar{\omega}_1}{\sqrt{\rho_c \Delta P_{c1}}} \quad (52a)$$

$$Y_2 C_2^* = \frac{\bar{\omega}_2}{\sqrt{\rho_c \Delta P_{c2}}} \quad (52b)$$

where $C_1^*$ and $C_2^*$ are pseudo discharge coefficients for the capillary tube 226 at the two preselected sample gas 12 flows $\bar{\omega}_1^*$ and $\bar{\omega}_2^*$. The molar flows $\bar{\omega}_1^*$ and $\bar{\omega}_2^*$ are determined in the molar flow meter 294 by measuring the time, $tm_1$ and $tm_2$ for the pressure in a fixed volume 295 to drop between two predetermined pressures. Accepting that $\bar{\omega}_1^*$ and $\bar{\omega}_2^*$ can be represented by $tm_1$ and $tm_2$ and dividing Eq. (52a) by Eq. (52b) results in:

$$\frac{Y_1 C_1^*}{Y_2 C_2^*} = \frac{tm_1}{tm_2} \sqrt{\frac{\Delta P_{c2}}{\Delta P_{c1}}} \quad (53)$$

The ratio of the pseudo capillary tube discharge coefficients $$\frac{Y_1 C_1^*}{Y_2 C_2^*} \qquad (5)$$

is assumed to be equal to the ratio of the actual capillary tube discharge coefficients $$\frac{Y_1 C_1}{Y_2 C_2}$$

for the two preselected flows, so:

$$\frac{Y_1 C_1}{Y_2 C_2} = \frac{tm_1}{tm_2}\sqrt{\frac{\Delta P_{c2}}{\Delta P_{c1}}} = \frac{Y_1}{Y_2}\frac{C_i + K_c f(R_{e1})}{C_i + K_c f(R_{e2})} \qquad (54)$$

where $R_{e1}$ and $R_{e2}$ are the Reynold's Numbers for the flow through the capillary tube 226 at the preselected flows. If the capillary tube 226 is a tortuous path capillary tube 226', which is preferred, the $K_c\, f(R_e)$ term in Eq. (54) is small compared to the $C_i$ term for the normal range of operating Reynold's Number. Moreover, the two preselected flows can be set in a ratio such that $R_{e2} = \eta R_{e1}$. The function $f(R_{e1})$, is then represented by:

$$f(R_{e1}) = \frac{C_i \frac{Y_2}{Y_1} \frac{tm_2}{tm_1}\sqrt{\frac{\Delta P_{c2}}{\Delta P_{c1}}} - 1}{1 - \frac{1}{\eta^{0.7}}} \qquad (55)$$

Equation (55) allows the calculation of the function $f(R_{e1})$ in real time without knowing the viscosity, $\mu$, of the sample gas 12.

The ratio of the Reynold's Number of the flow through the tortuous path capillary tube 226' compared to the flow through the orifice 222 is represented by:

$$\frac{R_{eD}}{R_{eC}} = S\frac{D_D}{D_C} \qquad (56)$$

where $D_C$ is the effective diameter of the tortuous path capillary tube 226' mounted on the pipeline 16 and $D_D$ is the effective diameter of the pipeline 16. It follows that the discharge coefficient ratio, $$\left(\frac{C_o}{C_c}\right) = C_r$$

is determined by solving Eq. (57) by iteration:

$$\left(\frac{C_o}{C_c}\right) = C_r = \qquad (57)$$

-continued $$\frac{C_{ic}\left[1 + \frac{K_c \frac{Y_2}{Y_1}\sqrt{\frac{\Delta P_{c2}}{\Delta P_{c1}}} - 1}{1 - \frac{1}{\eta^{0.7}}}\right]}{C_{io}\left[1 + \left(S\frac{D_D}{D_C}\right)\right]^{0.7} K_o \frac{C_{ic}}{C_{io}} \frac{Y_2}{Y_1}\sqrt{\frac{\Delta P_{c2}}{\Delta P_{c1}}} - 1}{1 - \frac{1}{\eta^{0.7}}}}$$

Equation (57) is solved by iteration because the solution to Eq. (57) depends on the splitting variable S and S as defined in Eq. (47) depends on $$\frac{C_o}{C_o} = C_r.$$

After the discharge coefficient ratio $$\left(\frac{C_o}{C_c}\right) = C_r$$

is determined by iteration, the splitting variable S is calculated in the control system 20 pursuant to Eq. (47).

Many modifications and variations of these preferred embodiments that are within the scope and spirit of the invention will be apparent to those with ordinary skill in the art.

I claim:

1. A method for measuring a base condition volumetric flowrate ($Q_b$) of a pipeline gas corresponding to a volumetric flowrate at a base condition pressure and temperature, the method comprising:

measuring a flowrate ($Q_f$) of the pipeline gas flowing through the pipeline with a pipeline gas flowmeter;

flowing a sample gas from the pipeline to a sample gas flowmeter;

measuring a flowrate ($Q_f'$) of the sample gas with the sample gas flowmeter;

maintaining the temperature of the sample gas at substantially the same temperature as the pipeline gas in the pipeline when the flowrate ($Q_f'$) of the sample gas is measured by the sample gas flowmeter;

measuring a base condition sample gas volumetric flowrate ($Q_b'$) by measuring a base condition energy flowrate of the sample gas ($E_{sample\ gas}$);

measuring a base condition heating value of the sample gas ($H_{sample\ gas}$); and dividing the base condition sample gas energy flowrate ($E_{sample\ gas}$) by the base condition sample gas heating value ($H_{sample\ gas}$); determining a correction ratio $$\left(\frac{Q_b'}{Q_f'}\right);$$

and determining the volumetric flowrate ($Q_b$) at base condition temperature and pressure by multiplying the flowrate ($Q_f$) of the pipeline gas by the correction ratio $$\left(\frac{Q_{b'}}{Q_{f'}}\right)$$

according to the relationship, $$Q_b = Q_f\left(\frac{Q_{b'}}{Q_{f'}}\right).$$

2. A method as recited in claim 1 further comprising the step of:
splitting the flow of sample gas flowing from the sample gas flowmeter into a waste stream and a test stream before measuring the base condition sample gas volumetric flowrate ($Q_{b}'$), wherein the base condition sample gas energy flowrate ($E_{sample\ gas}$) is measured by measuring a base condition energy flowrate of the test stream and multiplying the base condition energy flowrate of the test stream by a ratio of a mass flowrate of the sample gas flowing from the sample gas flowmeter compared to a mass flowrate of the test stream.

3. A method as recited in claim 2 further comprising the step of burning the waste stream in a catalytic burner.

4. A method as recited in claim 1 wherein the base condition sample gas heating value ($H_{sample\ gas}$) is measured by:
flowing the sample gas to a burner at a sample gas volumetric flowrate ($Q_{sample\ gas}$) and burning the sample gas with air flowed to the burner at a sample-gas air flowrate ($\omega_{air\ sample}$), the sample-gas air flowrate ($\omega_{air\ sample}$) being of such relative magnitude to the sample gas volumetric flowrate ($Q_{sample\ gas}$) so that the sample gas burns at maximum flame temperature;
intermittently flowing a reference gas to the burner at a reference gas volumetric flowrate ($Q_{reference\ gas}$) and burning the reference gas with air flowed to the burner at a reference-gas air flowrate ($\omega_{air\ reference}$), the reference-gas air flowrate ($\omega_{air\ reference}$) being of such relative magnitudes to the reference gas volumetric flowrate ($Q_{reference\ gas}$) so the reference gas burns at a maximum flame temperature; and
determining the base condition sample gas heating value ($H_{sample\ gas}$) using the following expression:

$$H_{sample\ gas} = H_{reference\ gas}\frac{(Q_{reference\ gas})}{(Q_{sample\ gas})}\frac{(\omega_{air\ sample})}{(\omega_{air\ reference})}$$

where $H_{reference\ gas}$ is a known heating value for the reference gas at the base condition pressure and temperature.

5. A method as recited in claim 4 wherein the ratio $$\left(\frac{Q_{reference\ gas}}{Q_{sample\ gas}}\right)$$

is determined by:
filling a chamber with sample gas;
flowing the sample gas from the chamber;
measuring a time rate of change of sample gas pressure $$\left(\frac{dP}{dt}\right)_{sample\ gas}$$

as the sample gas flows from the chamber at a measuring pressure;
filling the chamber with reference gas;
flowing the reference gas from the chamber;
measuring a time rate of change of reference gas pressure $$\left(\frac{dP}{dt}\right)_{reference\ gas}$$

as the reference gas flows form the chamber at substantially the same measuring pressure as the sample gas; and
dividing the time rate of change of the reference gas pressure $$\left(\frac{dP}{dt}\right)_{reference\ gas}$$

by the time rate of change of the sample gas pressure $$\left(\frac{dP}{dt}\right)_{sample\ gas}$$

to determine the ratio $$\left(\frac{Q_{reference\ gas}}{Q_{sample\ gas}}\right).$$

6. A method as recited in claim 1 wherein the base condition sample gas energy flowrate ($E_{sample\ gas}$) is measured by:
flowing sample gas from the sample gas flowmeter to a burner;
burning the sample gas in the burner with air flowing to the burner at an air flowrate ($\omega_{air}$);
adjusting the air flowrate ($\omega_{air}$) to the burner so that the sample gas burns at maximum flame temperature;
determining the adjusted air flowrate ($\omega_{air}$); and
determining the base condition sample gas energy flowrate ($E_{sample\ gas}$) using the following relation:

$$E_{sample\ gas} = K_{max-air}\omega_{air}$$

where $K_{max-air}$ is a constant.

7. A method as recited in claim 1 wherein the base condition sample gas energy flowrate ($E_{sample\ gas}$) is measured by:
flowing sample gas from the sample gas flowmeter;
burning the sample gas in a burner with air flowing to the burner at a constant air flowrate;
adjusting the flowrate of the sample gas to the burner so that the sample gas burns at maximum flame temperature;
determining the base condition sample gas energy flowrate ($E_{sample\ gas}$) using the following relation:

$$E_{sample\ gas} = K_{max-air}\Omega_{air}$$

where $K_{max-air}$ is a constant, and $\omega_{air}$ is the air flowrate.

8. A method as recited in claim 1 wherein the flowrate of the flowing sample gas ($Q_f$) is maintained at a substantially constant Reynold's Number and the base condition sample gas energy flowrate ($E_{sample\ gas}$) is measured by:

flowing the sample gas to a burner;
burning the sample gas in the burner with air;
adjusting the air flowrate ($\omega_{air}$) to the burner so that the sample gas burns at maximum flame temperature;
measuring the adjusted air flowrate ($\omega_{air}$); and
determining the base condition sample gas energy flowrate ($E_{sample\ gas}$) using the following relation:

$$E_{sample\ gas} = K_{max-air}\omega_{air}$$

where $K_{max-air}$ is a constant.

9. A volumetric flow corrector for adjusting a flowrate ($Q_f$) of a pipeline gas flowing through a pipeline to a pipeline gas base condition volumetric flowrate ($Q_b$) at a base condition pressure and temperature by applying a correction factor, the volumetric flow corrector comprising:

conduit means for flowing a sample gas from the pipeline;
first means for measuring a flowrate ($Q_f$) of the sample gas through the conduit means, the sample gas being maintained at substantially the same temperature as the pipeline gas in the pipeline when the first means measures the flowrate ($Q_f$) of the sample gas;
second means for measuring a base condition energy flowrate ($E_{sample\ gas}$) of the sample gas flowing through the conduit means;
third means for measuring a base condition heating value ($H_{sample\ gas}$) of the sample gas flowing through the conduit means;
control means, operably connected to the first, second and third means, for determining the correction factor from the sample gas flowrate ($Q_f$), the base condition energy flowrate ($E_{sample\ gas}$) of the sample gas, and the base condition heating value ($H_{sample\ gas}$) of the sample gas.

10. A volumetric flow corrector as recited in claim 9 further comprising:

a mass flow splitter for splitting the flow of sample gas flowing through the conduit means into a test stream and a waste stream after the first means measures the sample gas flowrate ($Q_f$) through the conduit means, wherein the second means measures the base condition energy flowrate of the sample gas by measuring the base condition energy flowrate of the test stream and multiplying the base condition energy flowrate of the test stream by a ratio of a mass flowrate of the sample gas flowing from the first means compared to a mass flowrate of the test stream.

11. A volumetric flow corrector as recited in claim 10 further comprising:

a catalytic burner for burning the sample gas in the waste stream.

12. A volumetric flow corrector as recited in claim 9 wherein the second means comprises:

means for burning the sample gas flowing through the conduit means from the first means with air flowing at an air flowrate ($\omega_{air}$) to form a flame burning at a flame temperature;
means for measuring the flame temperature; and
means for adjusting the air flowrate ($\omega_{air}$) so that the sample gas burns at a maximum flame temperature.

13. A volumetric flow corrector as recited in claim 9 wherein the second means comprises:

means for burning the sample gas flowing through the conduit means from the first means with air flowing at an air flowrate ($\omega_{air}$) to form a flame burning at a flame temperature;
means for measuring the flame temperature; and
means for adjusting the sample gas flowrate to the burner so that the sample gas burns at maximum flame temperature.

14. A volumetric flow corrector as recited in claim 9 wherein the third means comprises:

means for burning the sample gas flowing at a sample gas flowrate ($Q_{sample\ gas}$) with air flowing at a sample-gas air flowrate ($\omega_{air\ sample}$), the sample-gas air flowrate ($\omega_{air\ sample}$) being of such relative magnitude to the sample gas flowrate ($Q_{sample\ gas}$) so that the sample gas burns at maximum flame temperature; and
means for flowing a reference gas to the burner at a reference gas flowrate ($Q_{reference\ gas}$) and burned with air flowing to the burner at a reference-gas air flowrate ($\omega_{air\ reference}$), the reference-gas air flowrate ($\omega_{air\ reference}$) being of such relative magnitude to the reference gas flowrate ($Q_{reference\ gas}$) so that the reference gas burns at maximum flame temperature;
wherein the base condition heating value of the sample gas ($H_{sample\ gas}$) is determined in the control means by the following expression:

$$H_{sample\ gas} = H_{reference\ gas} \frac{(Q_{reference\ gas})}{(Q_{sample\ gas})} \frac{(\omega_{air\ sample})}{(\omega_{air\ reference})}$$

where ($H_{reference\ gas}$) is a known heating value for the reference gas at base condition pressure and temperature.

15. A volumetric flow corrector as recited in claim 9, further comprising:

means for measuring a flowrate ($Q_f$) of the pipeline gas flowing through the pipeline.

* * * * *

UNITED STATES PATENT AND TRADEMARK OFFICE
CERTIFICATE OF CORRECTION

PATENT NO. : 5,323,657
DATED : June 28, 1994
INVENTOR(S) : Vander Heyden, Wm. H.

It is certified that error appears in the above—identified patent and that said Letters Patent is hereby corrected as shown below:

Col. 9, line 59   "$\Omega$" should be --$\omega$--.

Col. 10, line 5   "$\Omega$" should be --$\omega$--.

Col. 10, line 8   "$\Omega$" should be --$\omega$--.

Col. 10, line 28  "$\Omega$" should be --$\omega$--.

Col. 10, line 32  "$\Omega$" should be --$\omega$--.

Col. 10, line 47  "$\Omega$" should be --$\omega$--.

Col. 11, line 34  "$\Omega$" should be --$\omega$--.

Col. 26, line 23  ";" should be --:--.

Col. 33, line 25  "1991" should be --1981--.

Col. 36, line 48  "$\bar{\omega}_1$" should be --$\bar{\omega}_1^*$--.

Col. 36, line 52  "$\bar{\omega}_2$" should be --$\bar{\omega}_2^*$--.

Signed and Sealed this

Eleventh Day of October, 1994

BRUCE LEHMAN

*Attest:*

*Attesting Officer*   *Commissioner of Patents and Trademarks*